United States Patent
Koishihara et al.

(10) Patent No.: US 10,724,093 B2
(45) Date of Patent: Jul. 28, 2020

(54) **MARKER ASSOCIATED WITH POWDERY MILDEW RESISTANCE IN PLANT OF GENUS *FRAGARIA* AND USE THEREOF**

(71) Applicant: TOYOTA JIDOSHA KABUSHIKI KAISHA, Toyota-shi, Aichi-ken (JP)

(72) Inventors: Hiroaki Koishihara, Nagoya (JP); Hiroyuki Enoki, Hamamatsu (JP); Masayoshi Muramatsu, Miyoshi (JP); Satoru Nishimura, Nagoya (JP); Susumu Yui, Morioka (JP); Masanori Honjo, Morioka (JP)

(73) Assignee: TOYOTA JIDOSHA KABUSHIKI KAISHA, Toyota-shi, Aichi (JP)

( * ) Notice: Subject to any disclaimer, the term of this patent is extended or adjusted under 35 U.S.C. 154(b) by 0 days.

(21) Appl. No.: 15/558,663

(22) PCT Filed: Mar. 18, 2016

(86) PCT No.: PCT/JP2016/058711
§ 371 (c)(1),
(2) Date: Sep. 15, 2017

(87) PCT Pub. No.: WO2016/148279
PCT Pub. Date: Sep. 22, 2016

(65) Prior Publication Data
US 2018/0112267 A1    Apr. 26, 2018

(30) Foreign Application Priority Data

Mar. 18, 2015 (JP) .................. 2015-054618
Mar. 4, 2016 (JP) .................. 2016-042028

(51) Int. Cl.
*C07H 21/04*    (2006.01)
*C12Q 1/68*    (2018.01)
*C12Q 1/6876*    (2018.01)
*C12Q 1/6895*    (2018.01)

(52) U.S. Cl.
CPC ......... *C12Q 1/6876* (2013.01); *C12Q 1/6895* (2013.01); *C12Q 2600/13* (2013.01); *C12Q 2600/156* (2013.01)

(58) Field of Classification Search
None
See application file for complete search history.

(56) References Cited

U.S. PATENT DOCUMENTS

2016/0201145 A1    7/2016 Enoki et al.

FOREIGN PATENT DOCUMENTS

WO    2015/034040 A1    3/2015

OTHER PUBLICATIONS

Lifshitz et al. (Proc. VIth Internat. Strawberry Symposium, Acta Hort. 842, ISHS 2009). (Year: 2009).*
Hirakawa et al. (DNA Research, vol. 21, pp. 169-181, Nov. 2013). (Year: 2013).*
Uchida, et al., Japanese Journal of Phytopathology, 1997, June, vol. 63, No. 3, 226 (142).
Yoshihisa Yamamoto et al., "Construction of Linkage Maps and Selection of DNA Markers for Powdery Mildew Resistance in Strawberries", Bull. Hyogo Pre. Tech. Cent. Agri. Forest Fish (Agriculture), 2003, pp. 7-12, vol. 51.
Shoko Isobe et al., "Ichigo no Rensa Chizu Sakusei to Udonkobyo Teikosei ni Kan'yo suru QTL Dotei", Horticultural Research, Sep. 24, 2011, p. 154, vol. 10, No. 2.
Uchida et al., Plant epidemic prevention, 1998, pp. 14-17, vol. 52.
"Summary of achievements, Miyagi Prefectural Agriculture and Horticulture Research Center", 2008.
Bulletin of Hyogo Prefectural Technology Center for Agriculture, Forestry and Fisheries, No. 51:7-12, Yamamoto et al., 2003.
International Search Report for PCT/JP2016/058711 dated Jun. 14, 2016.

* cited by examiner

*Primary Examiner* — Jeanine A Goldberg
(74) *Attorney, Agent, or Firm* — Sughrue Mion, PLLC

(57) ABSTRACT

This invention intends to develop many DNA markers for a plant of the genus *Fragaria* and detect powdery mildew resistance with high precision by using the many DNA markers. The marker associated with powdery mildew resistance in a plant of the genus *Fragaria* comprises a continuous nucleic acid region sandwiched between the nucleotide sequence as shown in SEQ ID NO: 1 and the nucleotide sequence as shown in SEQ ID NO: 19 in the chromosome of the plant of the genus *Fragaria*.

4 Claims, 28 Drawing Sheets
Specification includes a Sequence Listing.

Fig. 5-1

Phenotypes concerning powdery mildew resistance/susceptibility of hybrid progenies (F1) in Populations A, B, and E

| Miyazaki Natsu Haruka x 08 To-f | | Miyazaki Natsu Haruka x Ohkimi | | 09s E-b 45e x Miyazaki Natsu Haruka | |
|---|---|---|---|---|---|
| Lineage | Powdery mildew resistance | Lineage | Powdery mildew resistance | Lineage | Powdery mildew resistance |
| A01 | 0 | B01 | 0 | E01 | 0 |
| A02 | 1 | B02 | 0 | E02 | 1 |
| A03 | 1 | B03 | 0 | E03 | 1 |
| A04 | 0 | B04 | 1 | E04 | 1 |
| A05 | 1 | B05 | 0 | E05 | 1 |
| A06 | 0 | B06 | 0 | E06 | 0 |
| A07 | 0 | B07 | 1 | E07 | 0 |
| A08 | 1 | B08 | 0 | E08 | 0 |
| A09 | 1 | B09 | 0 | E09 | 0 |
| A10 | 1 | B10 | 1 | E10 | 0 |
| A11 | 0 | B11 | 1 | E11 | 1 |
| A12 | 0 | B12 | 0 | E12 | 1 |
| A13 | 0 | B13 | 1 | E13 | 0 |
| A14 | 0 | B14 | 1 | E14 | 0 |
| A15 | 0 | B15 | 1 | E15 | 1 |
| A16 | 0 | B16 | 1 | E16 | 1 |
| A17 | 1 | B17 | 0 | E17 | 0 |
| A18 | 1 | B18 | 0 | E18 | 0 |
| A19 | 1 | B19 | 0 | E19 | 0 |
| A20 | 0 | B20 | 0 | E20 | 0 |
| A21 | 1 | B21 | 0 | E21 | 0 |
| A22 | 0 | B22 | 1 | E22 | 0 |
| A23 | 0 | B23 | 0 | E23 | 1 |
| A24 | 1 | B24 | 1 | E24 | 1 |
| A25 | 1 | B25 | 1 | E25 | 1 |
| A26 | 0 | B26 | 0 | E26 | 1 |
| A27 | 1 | B27 | 0 | E27 | 1 |
| A29 | 1 | B28 | 1 | E28 | 1 |
| A30 | 1 | B29 | 0 | E29 | 1 |
| A31 | 1 | B30 | 1 | E30 | 0 |
| A32 | 1 | B31 | 1 | E31 | 0 |
| A33 | 1 | B32 | 0 | E32 | 0 |

*Fig. 5-2

| Miyazaki Natsu Haruka x 08 To-f | | Miyazaki Natsu Haruka x Ohkimi | | 09s E-b 45e x Miyazaki Natsu Haruka | |
|---|---|---|---|---|---|
| Lineage | Powdery mildew resistance | Lineage | Powdery mildew resistance | Lineage | Powdery mildew resistance |
| A34 | 1 | B33 | 1 | E33 | 0 |
| A35 | 0 | B34 | 1 | E34 | 1 |
| A36 | 1 | B35 | 0 | E35 | 1 |
| A37 | 0 | B36 | 1 | E36 | 1 |
| A38 | 0 | B37 | 1 | E37 | 1 |
| A39 | 0 | B38 | 0 | E38 | 0 |
| A40 | 0 | B39 | 0 | E39 | 1 |
| A41 | 0 | B40 | 0 | E40 | 0 |
| A42 | 1 | B41 | 1 | E41 | 0 |
| A43 | 1 | B42 | 0 | E42 | 1 |
| A44 | 0 | | | | |
| A45 | 0 | | | | |
| A46 | 1 | | | | |
| A47 | 0 | | | | |
| A48 | 0 | | | | |
| A49 | 0 | | | | |
| A50 | 1 | | | | |
| A51 | 0 | | | | |

Powdery mildew resistance: 0: Not affected; 1: Affected

Fig.6-1

| Linkage group | Marker name | Miyazaki Natsu Haruka | 08 To-f | F1 | | | | | | | | | |
|---|---|---|---|---|---|---|---|---|---|---|---|---|---|
| | | | | 1 | 2 | 3 | 4 | 5 | 6 | 7 | 8 | 9 | 10 |
| | IB535110 | 199 | 26660 | 24842 | 208 | 200 | 23260 | 250 | 27722 | 25370 | 238 | 205 | 26497 |
| | IB522828 | 543 | 7069 | 8093 | 761 | 673 | 8055 | 936 | 5854 | 7729 | 763 | 737 | 8666 |
| | IB559302 | 605 | 9286 | 11105 | 1110 | 837 | 10461 | 1215 | 8031 | 9881 | 973 | 873 | 10931 |
| | IB719784 | 580 | 7032 | 8543 | 838 | 646 | 8093 | 953 | 5791 | 7722 | 815 | 740 | 8827 |
| | IB508805 | 1099 | 12677 | 12565 | 13385 | 1167 | 11477 | 1097 | 13138 | 12347 | 1015 | 1487 | 13826 |
| | IB710861 | 337 | 18650 | 22355 | 501 | 330 | 24233 | 498 | 25865 | 24961 | 425 | 454 | 22266 |
| | IB713087 | 225 | 48711 | 44036 | 282 | 237 | 44736 | 245 | 46674 | 47013 | 239 | 311 | 40090 |
| 08 To-f1 linkage group | IB302484 | 3989 | 21780 | 20013 | 18057 | 3939 | 20318 | 3303 | 14997 | 18748 | 3304 | 5139 | 18413 |
| | IB503795 | 1955 | 36530 | 31494 | 30441 | 2359 | 32142 | 1724 | 28720 | 30816 | 2018 | 2636 | 29436 |
| | IB700262 | 1277 | 35877 | 31978 | 31396 | 1109 | 33664 | 920 | 29942 | 32891 | 1253 | 1812 | 31734 |
| | IB515566 | 257 | 15574 | 17659 | 17125 | 351 | 17446 | 295 | 15311 | 16098 | 328 | 533 | 330 |
| | IB526892 | 4276 | 54786 | 58495 | 55405 | 4869 | 54997 | 4489 | 59967 | 60237 | 4866 | 4123 | 4128 |
| | IB504834 | 473 | 34291 | 23397 | 23418 | 505 | 23207 | 437 | 22750 | 24756 | 659 | 450 | 291 |
| | IB509379 | 2089 | 48930 | 49368 | 51237 | 1595 | 45209 | 1545 | 50432 | 50588 | 1505 | 1475 | 1877 |
| | IB518714 | 4137 | 76260 | 36523 | 22813 | 4720 | 26777 | 4734 | 28985 | 553310 | 4864 | 5045 | 4141 |
| | IB522595 | 674 | 7849 | 6116 | 6673 | 1381 | 7009 | 937 | 5563 | 6715 | 843 | 1352 | 1048 |
| | IB712150 | 1695 | 66456 | 34123 | 21797 | 2179 | 26399 | 1838 | 28761 | 53616 | 2515 | 3248 | 2568 |
| | IB722030 | 387 | 25796 | 18780 | 17784 | 362 | 17611 | 327 | 17147 | 18460 | 426 | 382 | 269 |
| | IB726514 | 582 | 37290 | 14863 | 8562 | 878 | 10983 | 583 | 11969 | 28035 | 703 | 1294 | 855 |
| Powdery mildew phenotype | | Affected | Resistant | Resistant | Affected | Affected | Resistant | Affected | Resistant | Resistant | Affected | Affected | Affected |

Fig.6-2

| Linkage group | Marker name | F1 | | | | | | | | | |
|---|---|---|---|---|---|---|---|---|---|---|---|
| | | 11 | 12 | 13 | 14 | 15 | 16 | 17 | 18 | 19 | 20 |
| 08 To-f1 linkage group | IB535110 | 25077 | 25651 | 23214 | 24771 | 24570 | 26310 | 199 | 202 | 206 | 25320 |
| | IB522828 | 7511 | 9008 | 5811 | 6561 | 5708 | 9646 | 574 | 746 | 804 | 12014 |
| | IB559302 | 10487 | 11213 | 8369 | 9342 | 8615 | 12731 | 604 | 984 | 700 | 10868 |
| | IB719784 | 8415 | 8548 | 6420 | 7101 | 6195 | 10076 | 509 | 686 | 661 | 9052 |
| | IB508805 | 12369 | 12694 | 10625 | 10527 | 10919 | 10906 | 809 | 858 | 954 | 15271 |
| | IB710861 | 23235 | 17440 | 24325 | 25450 | 23458 | 22326 | 335 | 431 | 225 | 12972 |
| | IB713087 | 43361 | 43950 | 42882 | 48315 | 42190 | 42796 | 241 | 327 | 237 | 41776 |
| | IB302484 | 18184 | 19275 | 18891 | 18079 | 16989 | 17055 | 19108 | 2941 | 2587 | 17779 |
| | IB503795 | 31458 | 31036 | 30296 | 32061 | 31032 | 29962 | 33654 | 1525 | 1627 | 33565 |
| | IB700262 | 31160 | 30638 | 32516 | 34075 | 33197 | 33445 | 37431 | 1072 | 1018 | 29188 |
| | IB515566 | 16697 | 17301 | 18188 | 17550 | 17381 | 17635 | 19539 | 356 | 333 | 18857 |
| | IB526892 | 57577 | 62149 | 59909 | 59339 | 60279 | 56512 | 62304 | 3970 | 3818 | 61927 |
| | IB504834 | 22788 | 25454 | 23436 | 24854 | 23554 | 22636 | 24783 | 393 | 631 | 19486 |
| | IB509379 | 52095 | 49079 | 46615 | 47830 | 45914 | 47035 | 40048 | 994 | 1110 | 46390 |
| | IB518714 | 31751 | 31453 | 32879 | 51190 | 28346 | 35178 | 41992 | 3754 | 3158 | 36901 |
| | IB522595 | 5679 | 6081 | 6166 | 6235 | 5282 | 5827 | 6790 | 801 | 894 | 6942 |
| | IB712150 | 31087 | 30754 | 31843 | 49824 | 27705 | 34194 | 38835 | 2046 | 2117 | 34815 |
| | IB722030 | 16481 | 21131 | 15620 | 18257 | 16536 | 16704 | 20586 | 325 | 434 | 19645 |
| | IB726514 | 13462 | 12527 | 13949 | 24357 | 11441 | 14669 | 17971 | 684 | 753 | 15189 |
| Powdery mildew phenotype | | Resistant | Resistant | Resistant | Resistant | Resistant | Resistant | Affected | Affected | Affected | Resistant |

Fig.6-3

| Linkage group | Marker name | F1 | | | | | | | | |
|---|---|---|---|---|---|---|---|---|---|---|
| | | 21 | 22 | 23 | 24 | 25 | 26 | 27 | 29 | 30 |
| 08 To-f1 linkage group | IB535110 | 258 | 27869 | 24926 | 205 | 203 | 28091 | 200 | 256 | 200 |
| | IB522828 | 616 | 9816 | 9704 | 472 | 482 | 8270 | 488 | 441 | 526 |
| | IB559302 | 701 | 11804 | 10933 | 522 | 654 | 10470 | 627 | 538 | 636 |
| | IB719784 | 574 | 9543 | 8976 | 486 | 586 | 8317 | 547 | 458 | 508 |
| | IB508805 | 1018 | 13869 | 14313 | 800 | 840 | 13879 | 775 | 924 | 845 |
| | IB710861 | 260 | 24899 | 23080 | 244 | 315 | 22623 | 260 | 275 | 242 |
| | IB713087 | 259 | 42546 | 42699 | 215 | 202 | 44500 | 206 | 257 | 249 |
| | IB302484 | 3216 | 16893 | 18658 | 2124 | 3722 | 20797 | 4325 | 3695 | 4199 |
| | IB503795 | 1486 | 28339 | 30392 | 1298 | 2248 | 34916 | 2470 | 2246 | 2183 |
| | IB700262 | 853 | 30403 | 31029 | 1442 | 1239 | 36760 | 1322 | 1534 | 1287 |
| | IB515566 | 280 | 17033 | 18881 | 275 | 306 | 18829 | 345 | 294 | 287 |
| | IB526892 | 4020 | 64548 | 62282 | 5375 | 3396 | 57922 | 2848 | 3360 | 3130 |
| | IB504834 | 337 | 23549 | 25545 | 710 | 469 | 26843 | 500 | 305 | 352 |
| | IB509379 | 1050 | 50285 | 50467 | 991 | 1791 | 46704 | 949 | 1097 | 1439 |
| | IB518714 | 3402 | 41598 | 33675 | 4624 | 5022 | 42470 | 3844 | 3789 | 4511 |
| | IB522595 | 952 | 5319 | 6309 | 640 | 878 | 6287 | 715 | 553 | 1078 |
| | IB712150 | 2001 | 41474 | 33667 | 2804 | 2870 | 40837 | 2644 | 2011 | 2979 |
| | IB722030 | 301 | 17302 | 18266 | 395 | 362 | 21559 | 371 | 269 | 291 |
| | IB726514 | 711 | 19915 | 15323 | 845 | 958 | 20002 | 920 | 668 | 958 |
| Powdery mildew phenotype | | Affected | Resistant | Resistant | Affected | Affected | Resistant | Affected | Affected | Affected |

Fig.6-4

| Linkage group | Marker name | 31 | 32 | 33 | 34 | 35 | F1 36 | 37 | 38 | 39 | 40 |
|---|---|---|---|---|---|---|---|---|---|---|---|
| 08 To-f1 linkage group | IB535110 | 201 | 208 | 200 | 264 | 28161 | 251 | 23316 | 29131 | 25422 | 28024 |
| | IB522828 | 461 | 816 | 508 | 662 | 8688 | 646 | 8598 | 7578 | 7993 | 8470 |
| | IB559302 | 519 | 1052 | 680 | 949 | 10813 | 798 | 10245 | 10423 | 9680 | 10362 |
| | IB719784 | 445 | 747 | 601 | 670 | 8382 | 643 | 7628 | 7489 | 7405 | 7709 |
| | IB508805 | 843 | 756 | 834 | 738 | 13086 | 901 | 12437 | 13883 | 13275 | 14306 |
| | IB710861 | 243 | 467 | 258 | 325 | 23893 | 252 | 26776 | 22530 | 21540 | 21825 |
| | IB713087 | 226 | 211 | 210 | 264 | 43205 | 250 | 51545 | 44811 | 45307 | 45152 |
| | IB302484 | 4823 | 4860 | 4351 | 3245 | 19581 | 4430 | 19562 | 3947 | 19035 | 21295 |
| | IB503795 | 2718 | 3224 | 2340 | 1891 | 34874 | 2669 | 31619 | 2102 | 33998 | 32591 |
| | IB700262 | 1402 | 1579 | 1258 | 993 | 37284 | 1642 | 32317 | 1223 | 35116 | 31979 |
| | IB515566 | 354 | 388 | 305 | 283 | 20046 | 309 | 20773 | 344 | 18965 | 19749 |
| | IB526892 | 3785 | 3622 | 3812 | 3426 | 58896 | 3074 | 63603 | 3519 | 56423 | 55261 |
| | IB504834 | 445 | 777 | 358 | 470 | 25007 | 485 | 25708 | 397 | 25531 | 25394 |
| | IB509379 | 1388 | 1209 | 1310 | 1328 | 46374 | 1355 | 43335 | 3209 | 48045 | 51945 |
| | IB518714 | 4001 | 5305 | 3998 | 3407 | 36396 | 3491 | 47796 | 4859 | 52833 | 34317 |
| | IB522595 | 627 | 703 | 525 | 645 | 6018 | 672 | 7242 | 817 | 5997 | 5779 |
| | IB712150 | 2545 | 3465 | 2440 | 1753 | 34016 | 2220 | 43765 | 2468 | 49417 | 33640 |
| | IB722030 | 323 | 425 | 299 | 330 | 18672 | 335 | 20196 | 342 | 20896 | 19726 |
| | IB726514 | 868 | 1109 | 803 | 628 | 16481 | 827 | 23414 | 744 | 24442 | 15300 |
| Powdery mildew phenotype | | Affected | Affected | Affected | Affected | Resistant | Affected | Resistant | Resistant | Resistant | Resistant |

Fig.6-5

| Linkage group | Marker name | F1 | | | | | | | | | | | Concordance with phenotype |
|---|---|---|---|---|---|---|---|---|---|---|---|---|---|
| | | 41 | 42 | 43 | 44 | 45 | 46 | 47 | 48 | 49 | 50 | 51 | |
| | IB535110 | 27473 | 260 | 256 | 22280 | 21605 | 199 | 22499 | 23365 | 25024 | 267 | 24260 | 98.0% |
| | IB522828 | 8355 | 448 | 564 | 7669 | 6992 | 612 | 7395 | 5838 | 8500 | 601 | 8517 | 98.0% |
| | IB559302 | 10996 | 553 | 733 | 9431 | 9411 | 904 | 9585 | 9385 | 10876 | 736 | 9845 | 98.0% |
| | IB719784 | 8400 | 558 | 568 | 7224 | 7246 | 738 | 7108 | 7049 | 9034 | 627 | 8140 | 98.0% |
| | IB508805 | 11650 | 877 | 888 | 11372 | 11936 | 631 | 10127 | 9604 | 11393 | 695 | 12442 | 96.0% |
| | IB710861 | 29585 | 261 | 405 | 24921 | 24913 | 339 | 27218 | 24476 | 23600 | 268 | 22528 | 98.0% |
| | IB713087 | 48317 | 260 | 258 | 51569 | 51391 | 223 | 50601 | 47555 | 45433 | 268 | 45072 | 98.0% |
| | IB302484 | 20603 | 18573 | 3305 | 19356 | 20069 | 2633 | 17642 | 18400 | 21514 | 3776 | 21901 | 90.0% |
| 08 To-f1 linkage group | IB503795 | 34614 | 28546 | 1730 | 33394 | 32937 | 1508 | 30402 | 32932 | 33507 | 2118 | 34331 | 90.0% |
| | IB700262 | 36117 | 32505 | 991 | 36260 | 33186 | 884 | 33115 | 33518 | 36227 | 1146 | 36118 | 90.0% |
| | IB515566 | 21969 | 20531 | 328 | 20861 | 21646 | 266 | 20230 | 18420 | 15982 | 294 | 18933 | 92.0% |
| | IB526892 | 60917 | 59343 | 4217 | 61549 | 59842 | 4221 | 59445 | 57065 | 63463 | 4899 | 55956 | 92.0% |
| | IB504834 | 26913 | 26972 | 714 | 24230 | 26505 | 599 | 25489 | 25313 | 26986 | 826 | 26481 | 92.0% |
| | IB509379 | 39270 | 44816 | 3206 | 43882 | 40891 | 3916 | 42680 | 48721 | 49624 | 2303 | 44050 | 92.0% |
| | IB518714 | 45207 | 26949 | 4263 | 39708 | 34384 | 6057 | 39447 | 25379 | 47109 | 4546 | 42783 | 92.0% |
| | IB522595 | 7429 | 6027 | 727 | 6893 | 7043 | 600 | 5745 | 5595 | 6709 | 637 | 5958 | 92.0% |
| | IB712150 | 42688 | 27239 | 1777 | 39259 | 33033 | 2567 | 38126 | 24578 | 45737 | 1865 | 41580 | 92.0% |
| | IB722030 | 19719 | 20103 | 443 | 18910 | 19356 | 413 | 18076 | 16538 | 20596 | 442 | 19927 | 92.0% |
| | IB726514 | 21197 | 10997 | 636 | 18220 | 14623 | 820 | 16505 | 10632 | 20683 | 584 | 20455 | 92.0% |
| Powdery mildew phenotype | | Resistant | Affected | Affected | Resistant | Resistant | Affected | Resistant | Resistant | Resistant | Affected | Resistant | - |

•Fig. 7-1
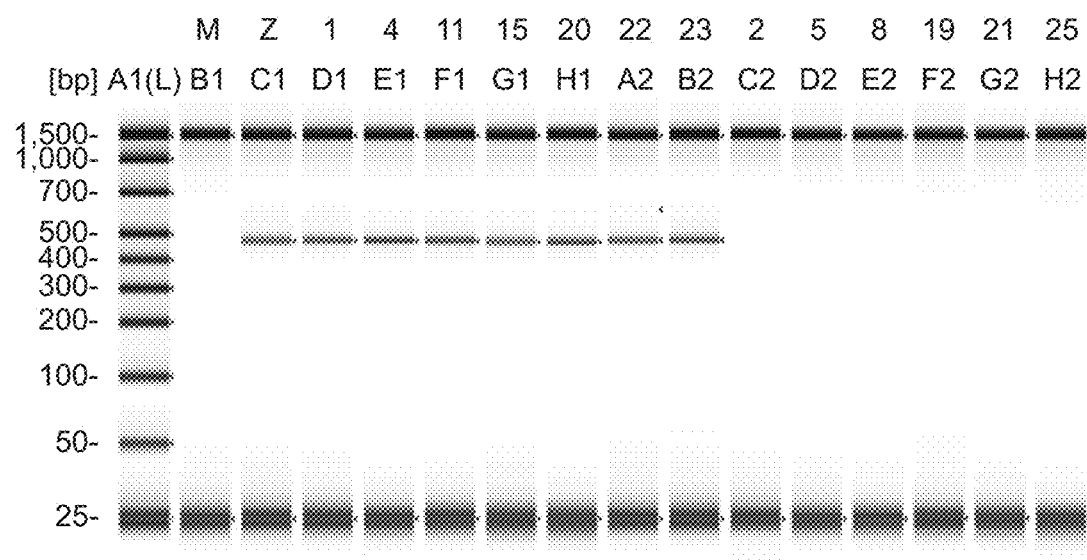
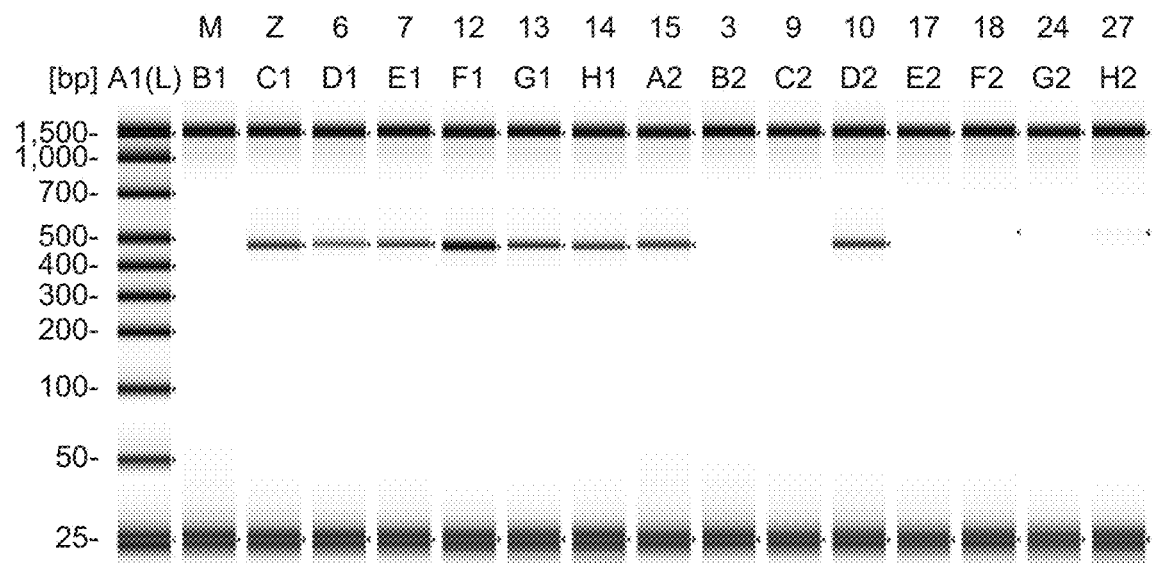

•Fig. 7-2
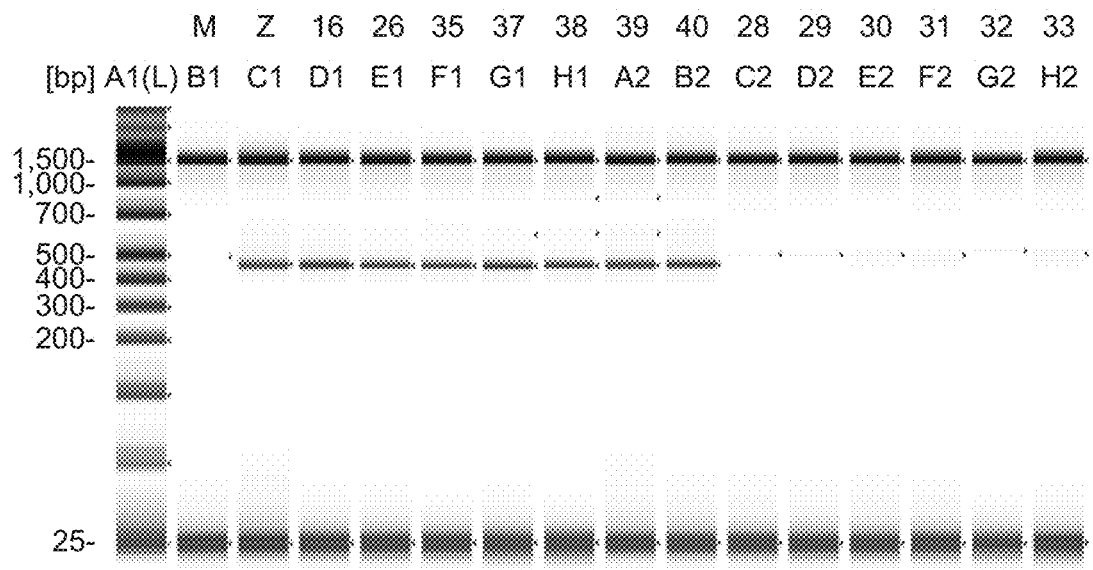
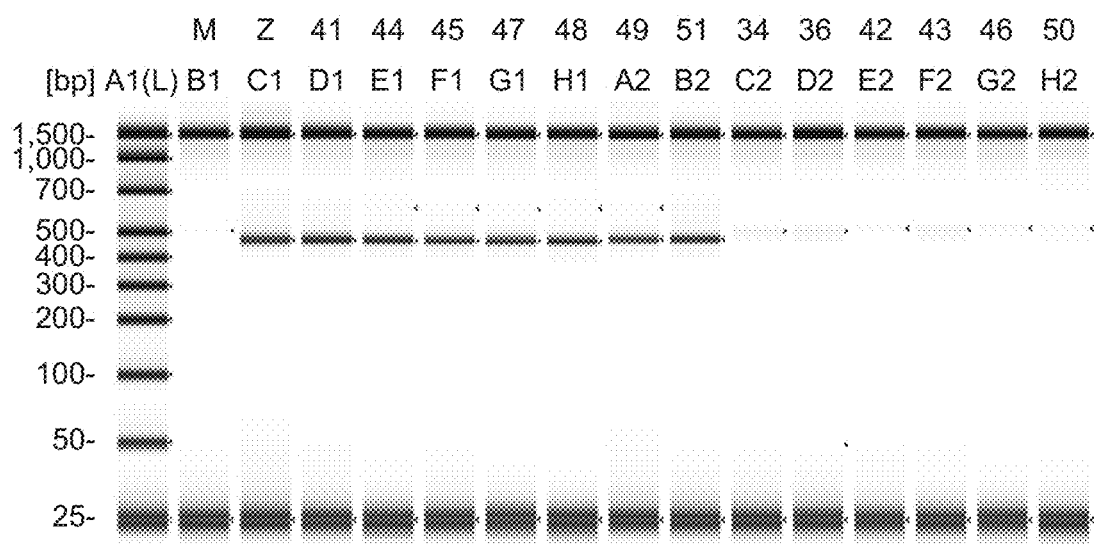

•Fig. 8-1
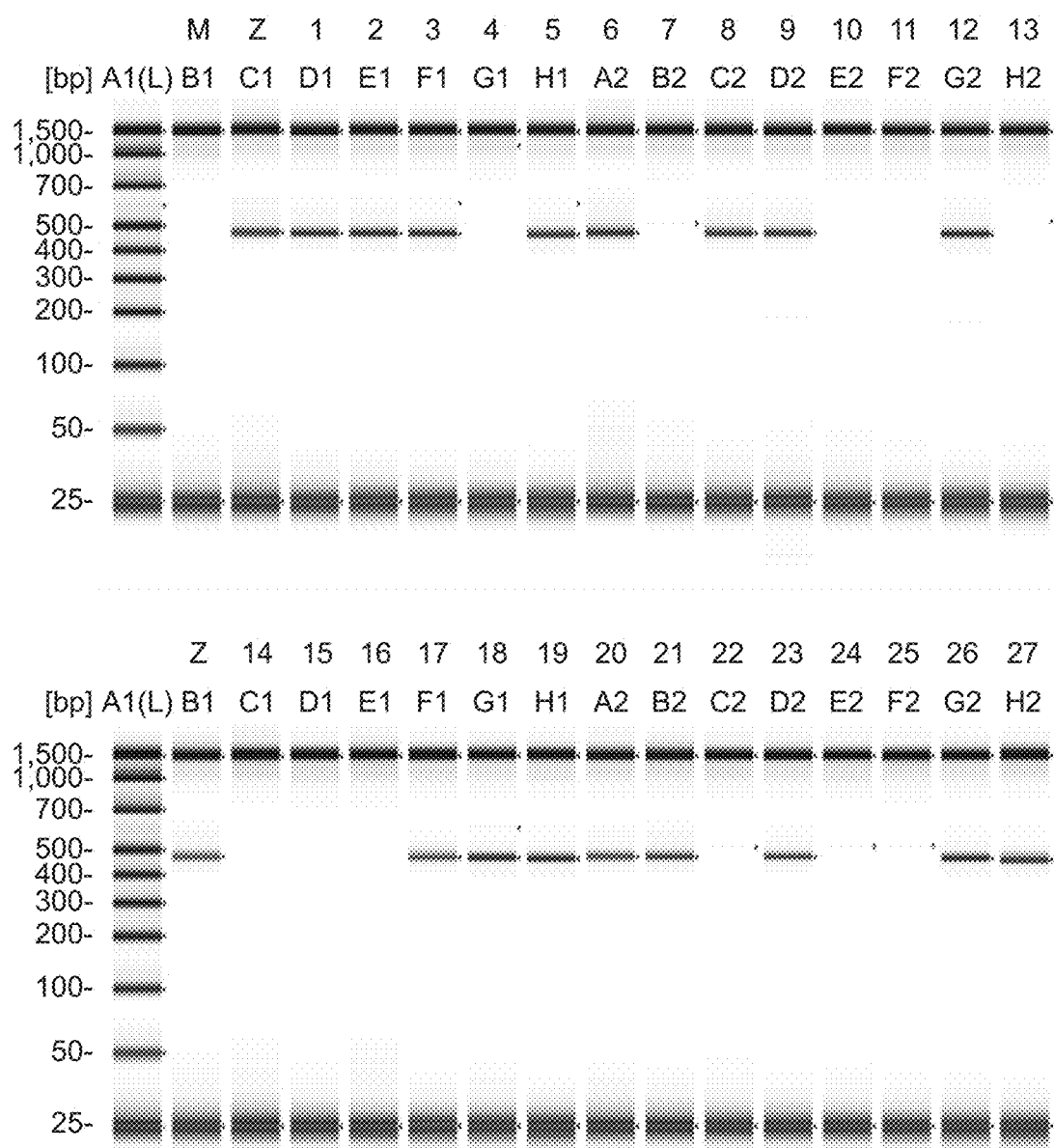

•Fig. 8-2
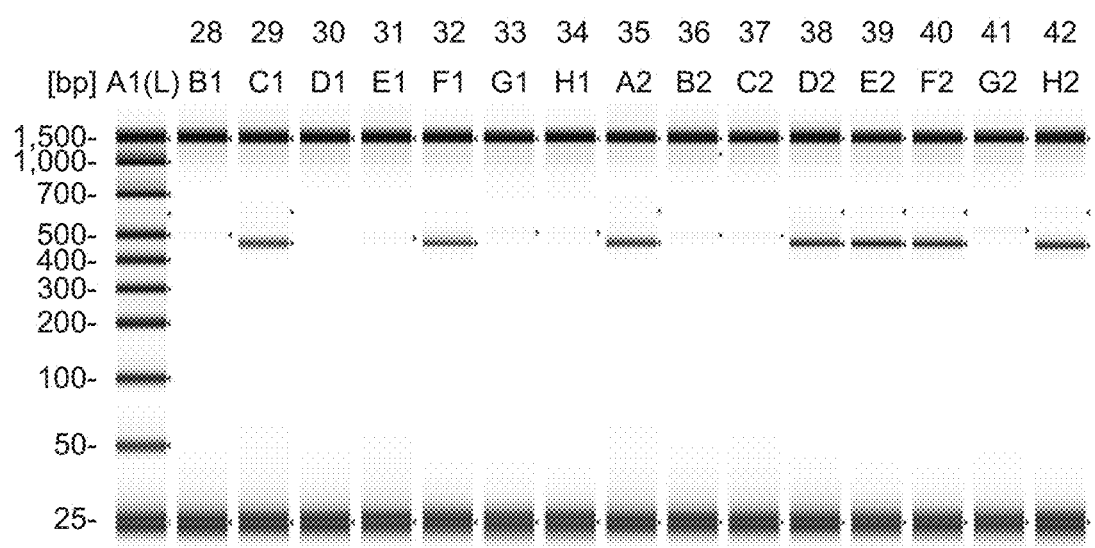

•Fig. 9-1
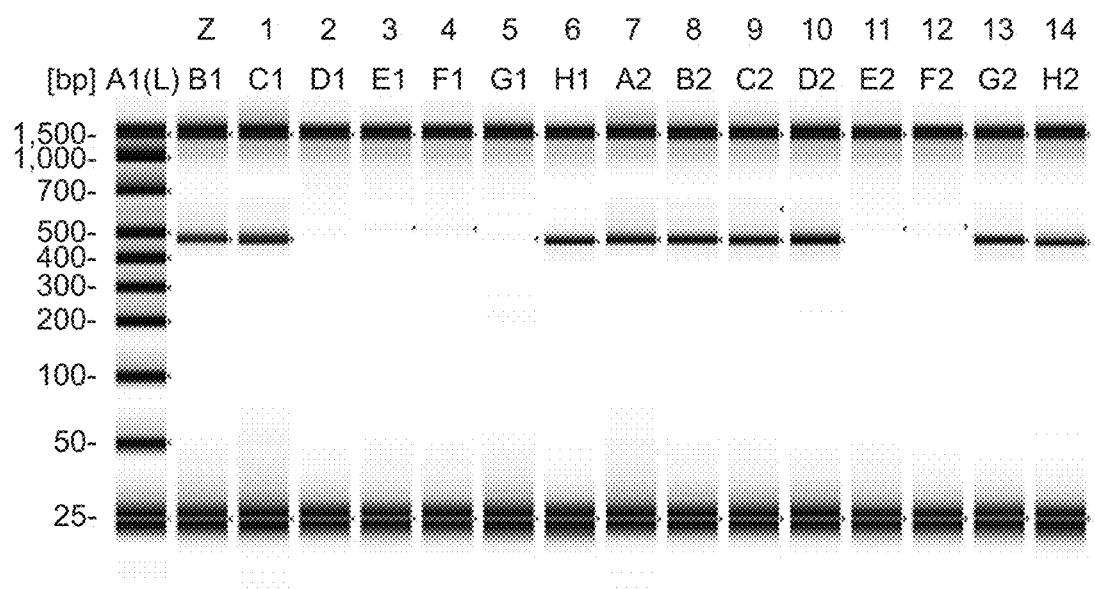
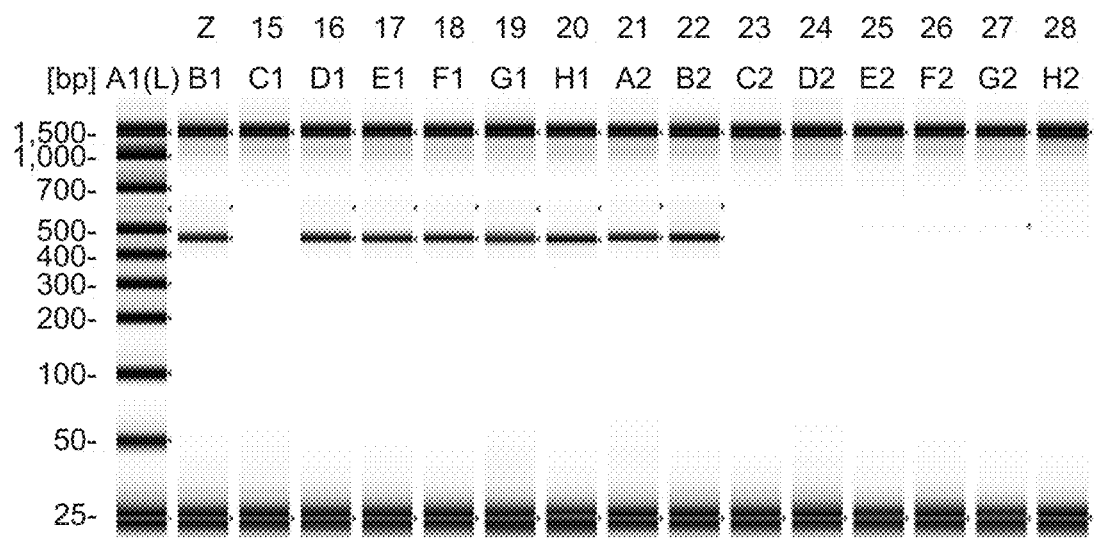

•Fig. 9-2
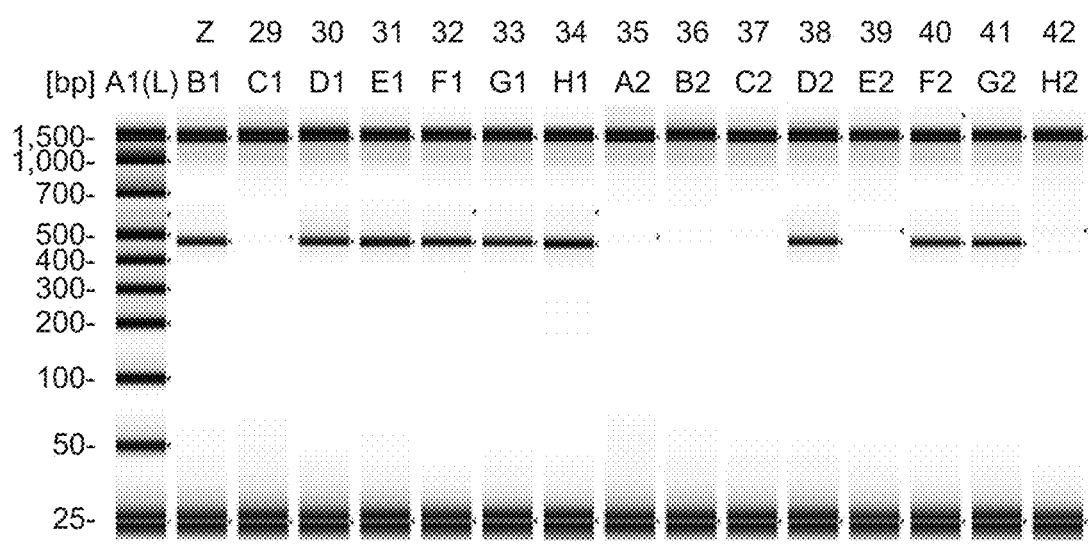

・Fig. 10-1

| Miyazaki Natsu Haruka x 08 To-f | | | Miyazaki Natsu Haruka x Ohkimi | | | 09s E-b 45e x Miyazaki Natsu Haruka | | |
|---|---|---|---|---|---|---|---|---|
| Lineage | Powdery mildew resistance | Results attained using PCR base marker | Lineage | Powdery mildew resistance | Results attained using PCR base marker | Lineage | Powdery mildew resistance | Results attained using PCR base marker |
| A01 | 0 | 0 | B01 | 0 | 0 | E01 | 0 | 0 |
| A02 | 1 | 1 | B02 | 0 | 0 | E02 | 1 | 1 |
| A03 | 1 | 1 | B03 | 0 | 0 | E03 | 1 | 1 |
| A04 | 0 | 0 | B04 | 1 | 1 | E04 | 1 | 1 |
| A05 | 1 | 1 | B05 | 0 | 0 | E05 | 1 | 1 |
| A06 | 0 | 0 | B06 | 0 | 0 | E06 | 0 | 0 |
| A07 | 0 | 0 | B07 | 1 | 1 | E07 | 0 | 0 |
| A08 | 1 | 1 | B08 | 0 | 0 | E08 | 0 | 0 |
| A09 | 1 | 1 | B09 | 0 | 0 | E09 | 0 | 0 |
| A10 | 1 | 0 | B10 | 1 | 1 | E10 | 0 | 0 |
| A11 | 0 | 0 | B11 | 1 | 1 | E11 | 1 | 1 |
| A12 | 0 | 0 | B12 | 0 | 0 | E12 | 1 | 1 |
| A13 | 0 | 0 | B13 | 1 | 1 | E13 | 0 | 0 |
| A14 | 0 | 0 | B14 | 1 | 1 | E14 | 0 | 0 |
| A15 | 0 | 0 | B15 | 1 | 1 | E15 | 1 | 1 |
| A16 | 0 | 0 | B16 | 1 | 1 | E16 | 1 | 0 |
| A17 | 1 | 1 | B17 | 0 | 0 | E17 | 0 | 0 |
| A18 | 1 | 1 | B18 | 0 | 0 | E18 | 0 | 0 |
| A19 | 1 | 1 | B19 | 0 | 0 | E19 | 0 | 0 |
| A20 | 0 | 0 | B20 | 0 | 0 | E20 | 0 | 0 |
| A21 | 1 | 1 | B21 | 0 | 0 | E21 | 0 | 0 |
| A22 | 0 | 0 | B22 | 1 | 1 | E22 | 0 | 0 |
| A23 | 0 | 0 | B23 | 0 | 0 | E23 | 1 | 1 |
| A24 | 1 | 1 | B24 | 1 | 1 | E24 | 1 | 1 |
| A25 | 1 | 1 | B25 | 1 | 1 | E25 | 1 | 1 |
| A26 | 0 | 0 | B26 | 0 | 0 | E26 | 1 | 1 |
| A27 | 1 | 1 | B27 | 0 | 0 | E27 | 1 | 1 |
| A29 | 1 | 1 | B28 | 1 | 1 | E28 | 1 | 1 |
| A30 | 1 | 1 | B29 | 0 | 0 | E29 | 1 | 1 |
| A31 | 1 | 1 | B30 | 1 | 1 | E30 | 0 | 0 |
| A32 | 1 | 1 | B31 | 1 | 1 | E31 | 0 | 0 |
| A33 | 1 | 1 | B32 | 0 | 0 | E32 | 0 | 0 |
| A34 | 1 | 1 | B33 | 1 | 1 | E33 | 0 | 0 |

•Fig. 10-2

| Miyazaki Natsu Haruka x 08 To-f | | | Miyazaki Natsu Haruka x Ohkimi | | | 09s E-b 45e x Miyazaki Natsu Haruka | | |
|---|---|---|---|---|---|---|---|---|
| Lineage | Powdery mildew resistance | Results attained using PCR base marker | Lineage | Powdery mildew resistance | Results attained using PCR base marker | Lineage | Powdery mildew resistance | Results attained using PCR base marker |
| A35 | 0 | 0 | B34 | 1 | 1 | E34 | 1 | 0 |
| A36 | 1 | 1 | B35 | 0 | 0 | E35 | 1 | 1 |
| A37 | 0 | 0 | B36 | 1 | 1 | E36 | 1 | 1 |
| A38 | 0 | 0 | B37 | 1 | 1 | E37 | 1 | 1 |
| A39 | 0 | 0 | B38 | 0 | 0 | E38 | 0 | 0 |
| A40 | 0 | 0 | B39 | 0 | 0 | E39 | 1 | 1 |
| A41 | 0 | 0 | B40 | 0 | 0 | E40 | 0 | 0 |
| A42 | 1 | 1 | B41 | 1 | 1 | E41 | 0 | 0 |
| A43 | 1 | 1 | B42 | 0 | 0 | E42 | 1 | 1 |
| A44 | 0 | 0 | | | | | | |
| A45 | 0 | 0 | | | | | | |
| A46 | 1 | 1 | | | | | | |
| A47 | 0 | 0 | | | | | | |
| A48 | 0 | 0 | | | | | | |
| A49 | 0 | 0 | | | | | | |
| A50 | 1 | 1 | | | | | | |
| A51 | 0 | 0 | | | | | | |

* Powdery mildew resistance: 0: Not affected; 1: Affected
* PCR base marker: 0: Band detected; 1: No band detected

•Fig. 11-1
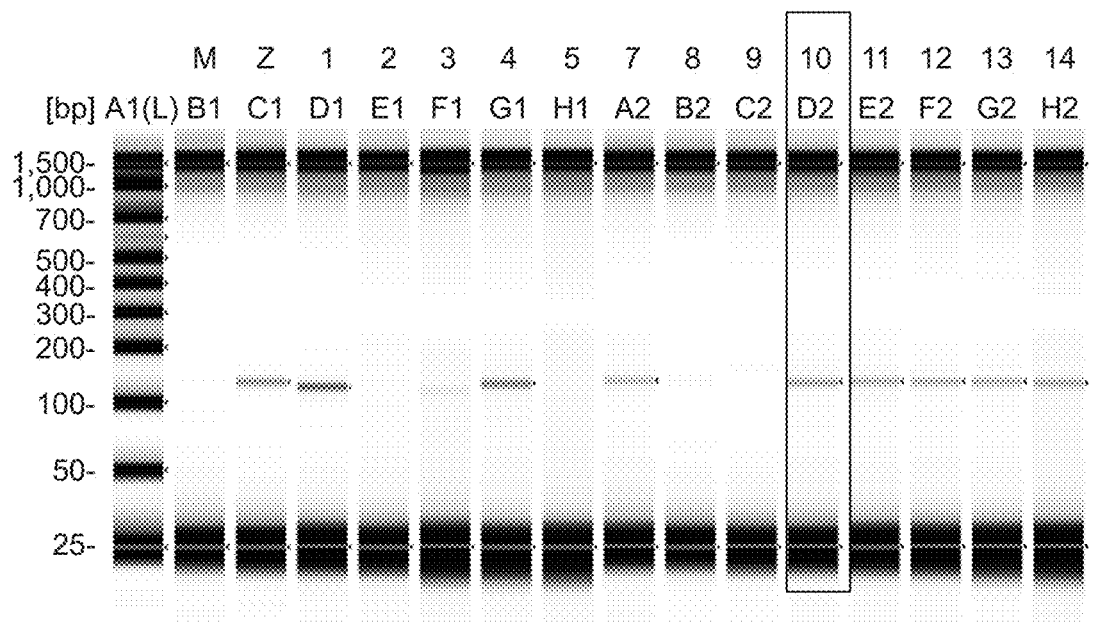
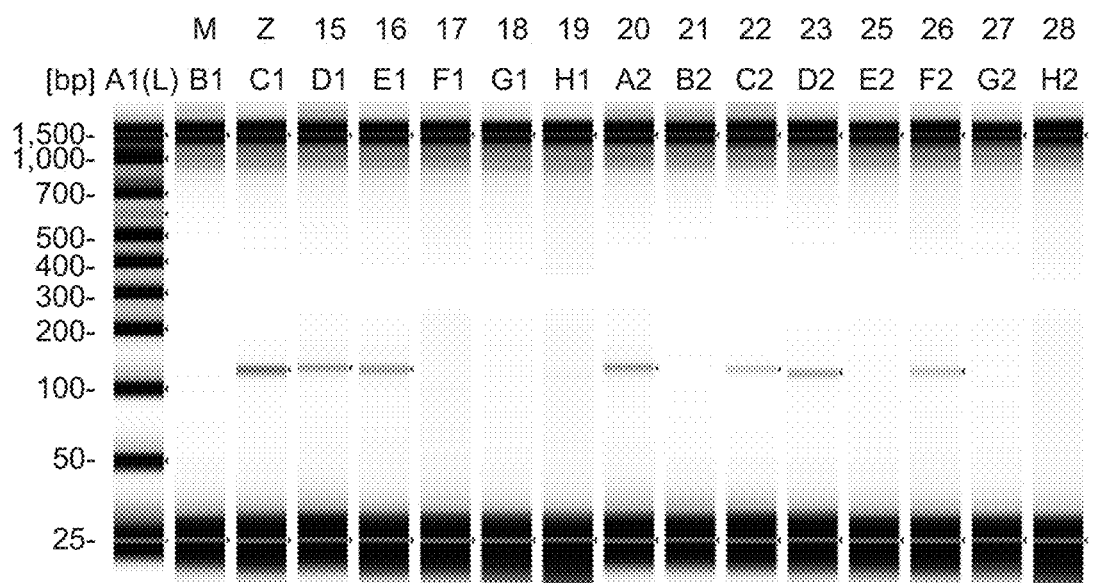

•Fig. 12-2
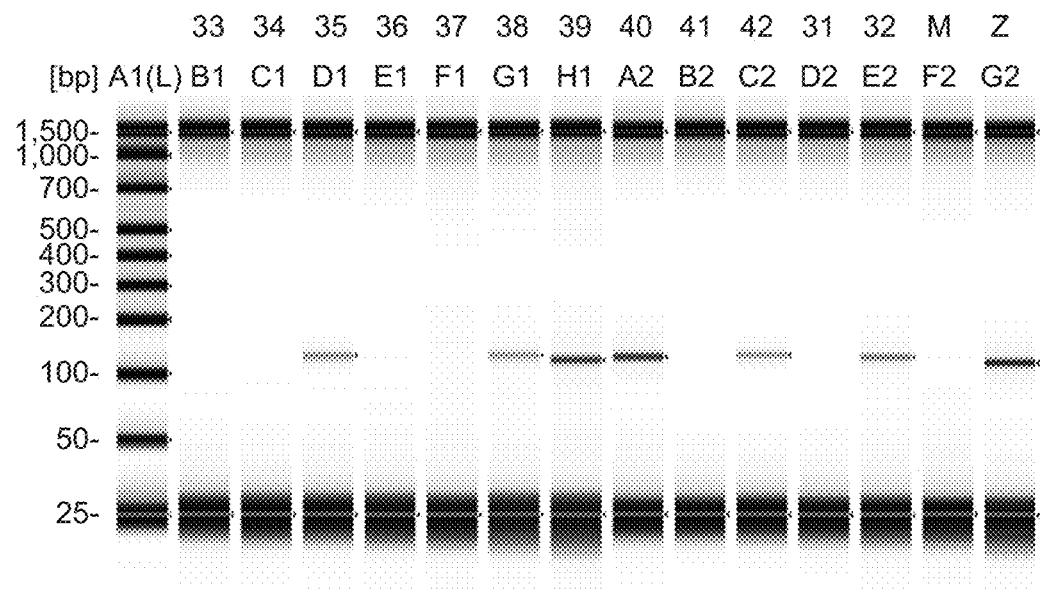
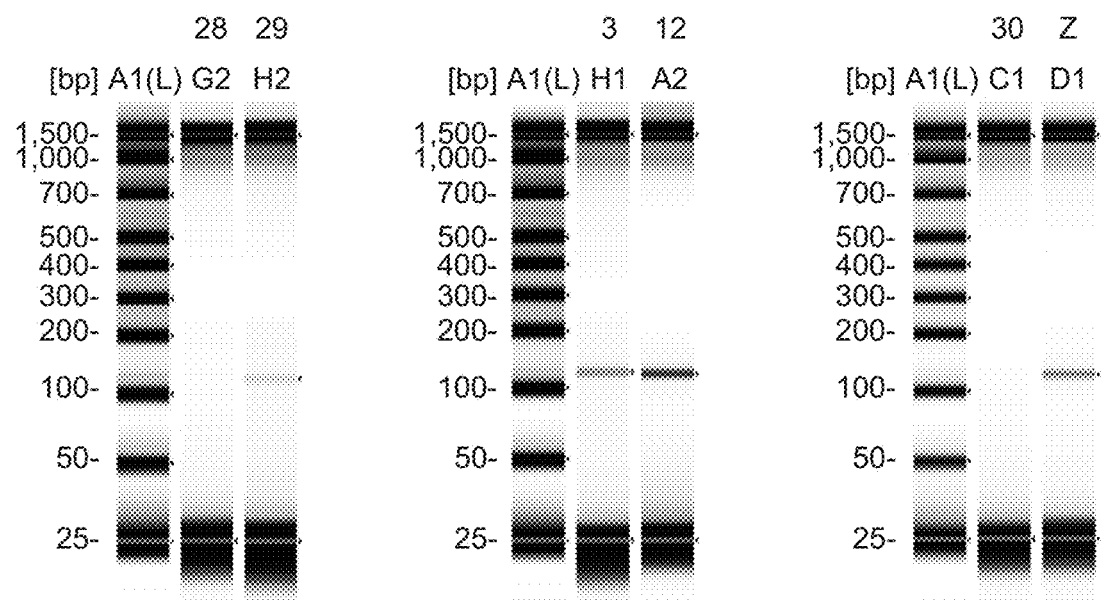

•Fig. 13-1
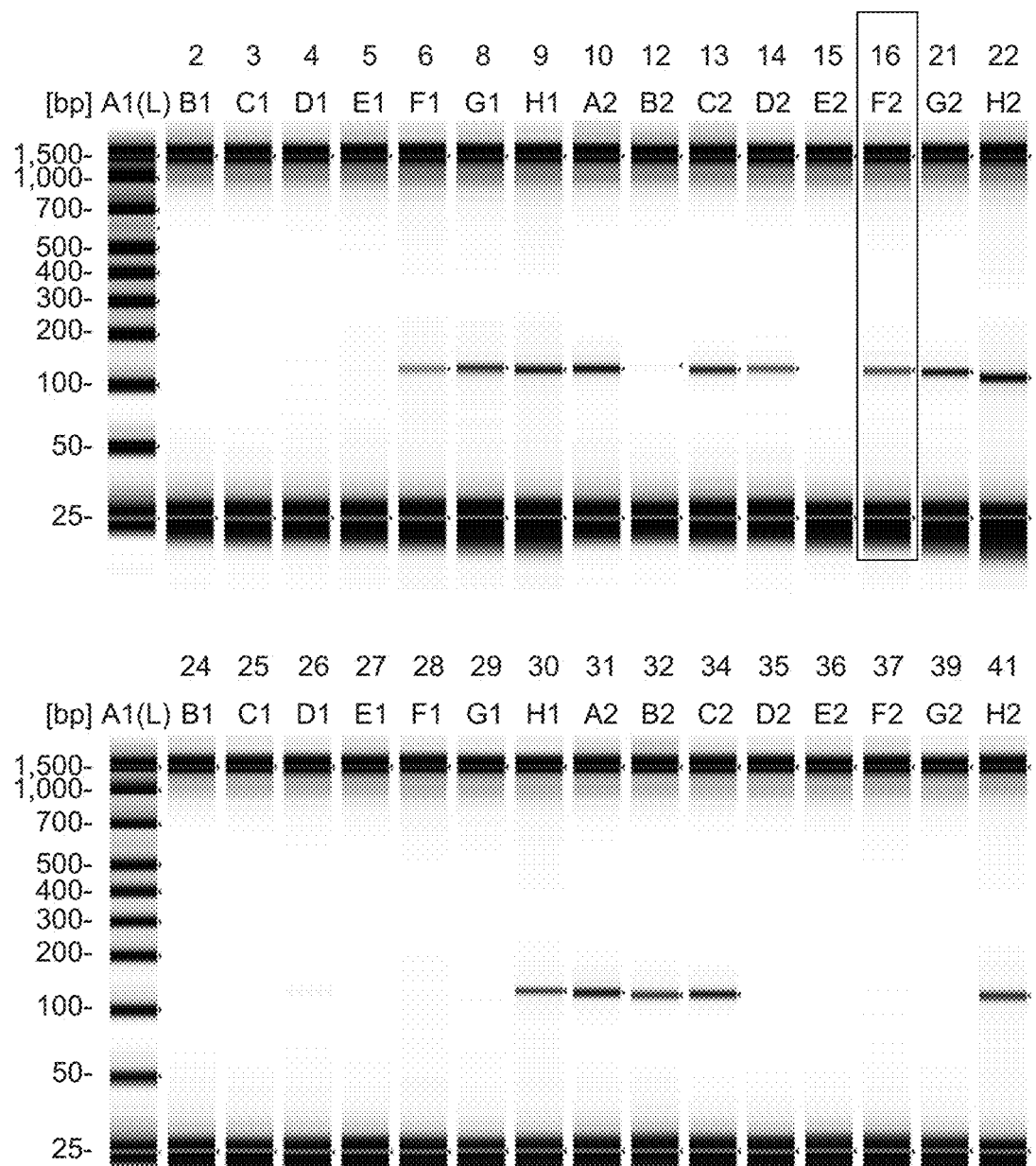

•Fig 14-1

| Miyazaki Natsu Haruka x 08 To-f | | | Miyazaki Natsu Haruka x Ohkimi | | | 09s E-b 45e x Miyazaki Natsu Haruka | | |
|---|---|---|---|---|---|---|---|---|
| Lineage | Powdery mildew resistance | Results attained using PCR base marker | Lineage | Powdery mildew resistance | Results attained using PCR base marker | Lineage | Powdery mildew resistance | Results attained using PCR base marker |
| A01 | 0 | 0 | B01 | 0 | 0 | E01 | 0 | 0 |
| A02 | 1 | 1 | B02 | 0 | 0 | E02 | 1 | 1 |
| A03 | 1 | 1 | B03 | 0 | 0 | E03 | 1 | 1 |
| A04 | 0 | 0 | B04 | 1 | 1 | E04 | 1 | 1 |
| A05 | 1 | 1 | B05 | 0 | 0 | E05 | 1 | 1 |
| A06 | 0 | 0 | B06 | 0 | 0 | E06 | 0 | 0 |
| A07 | 0 | 0 | B07 | 1 | 1 | E07 | 0 | 0 |
| A08 | 1 | 1 | B08 | 0 | 0 | E08 | 0 | 0 |
| A09 | 1 | 1 | B09 | 0 | 0 | E09 | 0 | 0 |
| A10 | 1 | 0 | B10 | 1 | 1 | E10 | 0 | 0 |
| A11 | 0 | 0 | B11 | 1 | 1 | E11 | 1 | 1 |
| A12 | 0 | 0 | B12 | 0 | 0 | E12 | 1 | 1 |
| A13 | 0 | 0 | B13 | 1 | 1 | E13 | 0 | 0 |
| A14 | 0 | 0 | B14 | 1 | 1 | E14 | 0 | 0 |
| A15 | 0 | 0 | B15 | 1 | 1 | E15 | 1 | 1 |
| A16 | 0 | 0 | B16 | 1 | 1 | E16 | 1 | 0 |
| A17 | 1 | 1 | B17 | 0 | 0 | E17 | 0 | 0 |
| A18 | 1 | 1 | B18 | 0 | 0 | E18 | 0 | 0 |
| A19 | 1 | 1 | B19 | 0 | 0 | E19 | 0 | 0 |
| A20 | 0 | 0 | B20 | 0 | 0 | E20 | 0 | 0 |
| A21 | 1 | 1 | B21 | 0 | 0 | E21 | 0 | 0 |
| A22 | 0 | 0 | B22 | 1 | 1 | E22 | 0 | 0 |
| A23 | 0 | 0 | B23 | 0 | 0 | E23 | 1 | 1 |
| A24 | 1 | 1 | B24 | 1 | 1 | E24 | 1 | 1 |
| A25 | 1 | 1 | B25 | 1 | 1 | E25 | 1 | 1 |
| A26 | 0 | 0 | B26 | 0 | 0 | E26 | 1 | 1 |
| A27 | 1 | 1 | B27 | 0 | 0 | E27 | 1 | 1 |
| A29 | 1 | 1 | B28 | 1 | 1 | E28 | 1 | 1 |
| A30 | 1 | 1 | B29 | 0 | 0 | E29 | 1 | 1 |
| A31 | 1 | 1 | B30 | 1 | 1 | E30 | 0 | 0 |
| A32 | 1 | 1 | B31 | 1 | 1 | E31 | 0 | 0 |
| A33 | 1 | 1 | B32 | 0 | 0 | E32 | 0 | 0 |
| A34 | 1 | 1 | B33 | 1 | 1 | E33 | 0 | 0 |

• Fig 14-2

| Miyazaki Natsu Haruka x 08 To-f | | | Miyazaki Natsu Haruka x Ohkimi | | | 09s E-b 45e x Miyazaki Natsu Haruka | | |
|---|---|---|---|---|---|---|---|---|
| Lineage | Powdery mildew resistance | Results attained using PCR base marker | Lineage | Powdery mildew resistance | Results attained using PCR base marker | Lineage | Powdery mildew resistance | Results attained using PCR base marker |
| A35 | 0 | 0 | B34 | 1 | 1 | E34 | 1 | 0 |
| A36 | 1 | 1 | B35 | 0 | 0 | E35 | 1 | 1 |
| A37 | 0 | 0 | B36 | 1 | 1 | E36 | 1 | 1 |
| A38 | 0 | 0 | B37 | 1 | 1 | E37 | 1 | 1 |
| A39 | 0 | 0 | B38 | 0 | 0 | E38 | 0 | 0 |
| A40 | 0 | 0 | B39 | 0 | 0 | E39 | 1 | 1 |
| A41 | 0 | 0 | B40 | 0 | 0 | E40 | 0 | 0 |
| A42 | 1 | 1 | B41 | 1 | 1 | E41 | 0 | 0 |
| A43 | 1 | 1 | B42 | 0 | 0 | E42 | 1 | 1 |
| A44 | 0 | 0 | | | | | | |
| A45 | 0 | 0 | | | | | | |
| A46 | 1 | 1 | | | | | | |
| A47 | 0 | 0 | | | | | | |
| A48 | 0 | 0 | | | | | | |
| A49 | 0 | 0 | | | | | | |
| A50 | 1 | 1 | | | | | | |
| A51 | 0 | 0 | | | | | | |

* Powdery mildew resistance: 0: Not affected; 1: Affected
* PCR base marker: 0: Band detected; 1: No band detected

MARKER ASSOCIATED WITH POWDERY MILDEW RESISTANCE IN PLANT OF GENUS *FRAGARIA* AND USE THEREOF

CROSS REFERENCE TO RELATED APPLICATIONS

This application is a National Stage of International Application No. PCT/JP2016/058711 filed Mar. 18, 2016, claiming priority based on Japanese Patent Application Nos. 2015-054618 filed Mar. 18, 2015 and 2016-042028 filed Mar. 4, 2016, the contents of all of which are incorporated herein by reference in their entirety.

Please replace the Sequence Listing submitted in International Application No. PCT/JP2016/058711 with the substitute Sequence Listing submitted herewith.

TECHNICAL FIELD

The present invention relates to a marker associated with powdery mildew resistance that enables selection of a plant line of the genus *Fragaria* exhibiting resistance against powdery mildew and use thereof.

BACKGROUND ART

With the development of DNA markers (also referred to as genetic markers or gene markers), both useful and undesirable traits can be rapidly and efficiently identified when improvement in plant varieties is intended. The development of DNA markers has advanced for a wide variety of practical plants as well as for model plants such as *Arabidopsis thaliana* and *Oryza sativa*. Thus, such markers significantly contribute to improvement in plant varieties.

Plant epidemic prevention 52: 14-17, Uchida, Inoue, 1998 reports that there are at least 2 pathogenic races of powdery mildew fungi of strawberries in Japan. Also, Plant epidemic prevention 52: 14-17, Uchida, Inoue, 1998 implies that, on the basis of the results of investigation concerning sensitivity and resistance to powdery mildew fungi, powdery mildew resistance of strawberries is controlled by at least one oligogene. However, Plant epidemic prevention 52: 14-17, Uchida, Inoue, 1998 does not disclose or suggest DNA markers associated with powdery mildew resistance of strawberries.

Bulletin of the Hyogo Prefectural Technology Center for Agriculture, Forestry and Fisheries, No. 51: 7-12, Yamamoto et al., 2003 discloses that a linkage map was prepared with the use of hybrid lines of strawberry varieties "Toyonoka" and "Houkou-wase" and DNA markers detecting powdery mildew resistance were selected. Bulletin of the Hyogo Prefectural Technology Center for Agriculture, Forestry and Fisheries, No. 51: 7-12, Yamamoto et al., 2003 discloses that 29 linkage groups of "Toyonoka"-specific markers (a total of 109 markers, full-length: 1451.7 cM) and 21 linkage groups of "Houkou-wase"-specific markers (a total of 88 markers, full-length: 1205.7 cM) were obtained and that QTL analysis was conducted on the basis of the results of investigation concerning the onset of powdery mildew. According to Bulletin of the Hyogo Prefectural Technology Center for Agriculture, Forestry and Fisheries, No. 51: 7-12, Yamamoto et al., 2003, however, the LOD value attained by prospective linkage groups is about 1.22.

Summary of achievements, Miyagi Prefectural Agriculture and Horticulture Research Center, Chiba, Itabashi, 2008 discloses that resistance to strawberry powdery mildew can be attained via aggregation of a plurality of resistant genes and that linkage maps of 30 linkage groups (137 DNA markers, full length: 1,360 cM) were prepared with the use of *F. virginiana* (the original species) having resistance to strawberry powdery mildew-afflicted variety "Sachinoka." According to Summary of achievements, Miyagi Prefectural Agriculture and Horticulture Research Center, Chiba, Itabashi, 2008, QTLs are designated at 3 positions as a result of the QTL analysis using the results of examination and linkage maps of strawberry powdery mildew.

SUMMARY OF THE INVENTION

Objects to be Attained by the Invention

To date, the DNA marker technologies concerning powdery mildew resistance of strawberries as described above could not be regarded as sufficient in terms of the logarithm of odds (LOD) and the contribution ratio, and such markers could not be evaluated as excellent markers.

Under the above circumstances, it is an object of the present invention to develop many DNA markers in plants of the genus *Fragaria*, which are polyploids with complex genomic structures, and to provide markers associated with powdery mildew resistance that enable evaluation of powdery mildew resistance with high accuracy with the use of such many DNA markers and to provide a method of using such markers.

Means for Attaining the Objects

The present inventors have conducted concentrated studies in order to attain the above objects. As a result, they discovered markers linked to powdery mildew resistance by preparing many markers in plants of the genus *Fragaria* and conducting linkage analysis between phenotypic expression and markers in hybrid progeny lines. This has led to the completion of the present invention.

The present invention includes the following.

(1) A marker associated with powdery mildew resistance in plants of the genus *Fragaria* comprising a continuous nucleic acid region sandwiched between the nucleotide sequence as shown in SEQ ID NO: 1 and the nucleotide sequence as shown in SEQ ID NO: 19 in the chromosome of the plant of the genus *Fragaria*.

(2) The marker associated with powdery mildew resistance in plants of the genus *Fragaria* according to (1), wherein the nucleic acid region comprises any nucleotide sequence selected from the group consisting of nucleotide sequences as shown in SEQ ID NOs: 1 to 19 or a part of the nucleotide sequence.

(3) The marker associated with powdery mildew resistance in plants of the genus *Fragaria* according to (1), wherein the nucleic acid region is located in a region sandwiched between the nucleotide sequence as shown in SEQ ID NO: 1 and the nucleotide sequence as shown in SEQ ID NO: 7 in the chromosome of the plant of the genus *Fragaria*.

(4) A method for producing a plant line of the genus *Fragaria* with improved powdery mildew resistance comprising:

a step of extracting a chromosome of a progeny plant whose at least one parent is a plant of the genus *Fragaria* and/or a chromosome of the parent plant of the genus *Fragaria*; and a step of determining the presence or absence of the marker associated with powdery mildew resistance in the plant of the genus *Fragaria* according to any one of (1) to (3) in the chromosome obtained above.

(5) The method for producing a plant line of the genus *Fragaria* according to (4), wherein the step of determination comprises conducting a nucleic acid amplification reaction using a primer that specifically amplifies the marker associated with powdery mildew resistance in the plant of the genus *Fragaria* to determine the presence or absence of the marker associated with powdery mildew resistance in the plant of the genus *Fragaria*.

(6) The method for producing a plant line of the genus *Fragaria* according to (4), wherein the step of determination involves the use of a DNA chip comprising a probe corresponding to the marker associated with powdery mildew resistance in the plant of the genus *Fragaria*.

(7) The method for producing a plant line of the genus *Fragaria* according to (4), wherein the progeny plant is a seed or seedling and the chromosome is extracted from the seed or seedling.

This description includes part or all of the content as disclosed in the descriptions and/or drawings of Japanese Patent Application Nos. 2015-054618 and 2016-042028, which are priority documents of the present application.

Effects of the Invention

The present invention provides novel markers associated with powdery mildew resistance in plants of the genus *Fragaria* that are linked to powdery mildew resistance among various traits of plants of the genus *Fragaria*. With the use of the markers associated with powdery mildew resistance in plants of the genus *Fragaria* according to the present invention, powdery mildew resistance in hybrid lines of the plants of the genus *Fragaria* can be tested. Thus, plant lines of the genus *Fragaria* with improved powdery mildew resistance can be identified in a very cost-effective manner.

BRIEF DESCRIPTION OF THE DRAWINGS

FIG. 5-1 shows a characteristic diagram showing the results of inspection concerning the onset and extent of powdery mildew in hybrid progeny lines of "Miyazaki Natsu Haruka" and "08 To-f" (Population A), hybrid progeny lines of "Miyazaki Natsu Haruka" and "Ohkimi" (Population B), and hybrid progeny lines of "Miyazaki Natsu Haruka" and "09s E-b 45e" (Population E).

FIG. 5-2 shows a characteristic diagram showing the results of inspection concerning the onset and extent of powdery mildew in hybrid progeny lines of "Miyazaki Natsu Haruka" and "08 To-f" (Population A), hybrid progeny lines of "Miyazaki Natsu Haruka" and "Ohkimi" (Population B), and hybrid progeny lines of "Miyazaki Natsu Haruka" and "09s E-b 45e" (Population E).

FIG. 6-1 shows a characteristic diagram showing the results of comparison of the array signal values of the markers associated with powdery mildew resistance of strawberries and the phenotypes of hybrid progeny lines of "Miyazaki Natsu Haruka" and "08 To-f" (Population A).

FIG. 6-2 shows a characteristic diagram showing the results of comparison of the array signal values of the markers associated with powdery mildew resistance of strawberries and the phenotypes of hybrid progeny lines of "Miyazaki Natsu Haruka" and "08 To-f" (Population A).

FIG. 6-3 shows a characteristic diagram showing the results of comparison of the array signal values of the markers associated with powdery mildew resistance of strawberries and the phenotypes of hybrid progeny lines of "Miyazaki Natsu Haruka" and "08 To-f" (Population A).

FIG. 6-4 shows a characteristic diagram showing the results of comparison of the array signal values of the markers associated with powdery mildew resistance of strawberries and the phenotypes of hybrid progeny lines of "Miyazaki Natsu Haruka" and "08 To-f" (Population A).

FIG. 6-5 shows a characteristic diagram showing the results of comparison of the array signal values of the markers associated with powdery mildew resistance of strawberries and the phenotypes of hybrid progeny lines of "Miyazaki Natsu Haruka" and "08 To-f" (Population A).

FIG. 7-1 shows electrophoresis images showing the results of PCR carried out with the use of a primer that specifically amplifies the marker IB535110 of hybrid progeny lines of "Miyazaki Natsu Haruka" and "08 To-f" (Population A).

FIG. 7-2 shows electrophoresis images showing the results of PCR carried out with the use of a primer that specifically amplifies the marker IB535110 of hybrid progeny lines of "Miyazaki Natsu Haruka" and "08 To-f" (Population A).

FIG. 8-1 shows electrophoresis images showing the results of PCR carried out with the use of a primer that specifically amplifies the marker IB535110 of hybrid progeny lines of "Miyazaki Natsu Haruka" and "Ohkimi" (Population B).

FIG. 8-2 shows electrophoresis images showing the results of PCR carried out with the use of a primer that specifically amplifies the marker IB535110 of hybrid progeny lines of "Miyazaki Natsu Haruka" and "Ohkimi" (Population B).

FIG. 9-1 shows electrophoresis images showing the results of PCR carried out with the use of a primer that specifically amplifies the marker IB535110 of hybrid progeny lines of "Miyazaki Natsu Haruka" and "09s E-b 45e" (Population E).

FIG. 9-2 shows electrophoresis images showing the results of PCR carried out with the use of a primer that specifically amplifies the marker IB535110 of hybrid progeny lines of "Miyazaki Natsu Haruka" and "09s E-b 45e" (Population E).

FIG. 10-1 shows a characteristic diagram summarizing the results of PCR carried out with the use of a primer that specifically amplifies the marker IB535110 of hybrid progeny lines of "Miyazaki Natsu Haruka" and "08 To-f" (Population A), hybrid progeny lines of "Miyazaki Natsu Haruka" and "Ohkimi" (Population B), and hybrid progeny lines of "Miyazaki Natsu Haruka" and "09s E-b 45e" (Population E).

FIG. 10-2 shows a characteristic diagram summarizing the results of PCR carried out with the use of a primer that specifically amplifies the marker IB535110 of hybrid progeny lines of "Miyazaki Natsu Haruka" and "08 To-f" (Population A), hybrid progeny lines of "Miyazaki Natsu Haruka" and "Ohkimi" (Population B), and hybrid progeny lines of "Miyazaki Natsu Haruka" and "09s E-b 45e" (Population E).

FIG. 11-1 shows electrophoresis images showing the results of PCR carried out with the use of a primer that specifically amplifies the marker IB522828 of hybrid progeny lines of "Miyazaki Natsu Haruka" and "08 To-f" (Population A).

FIG. 11-2 shows electrophoresis images showing the results of PCR carried out with the use of a primer that specifically amplifies the marker IB522828 of hybrid progeny lines of "Miyazaki Natsu Haruka" and "08 To-f" (Population A).

FIG. 11-3 shows electrophoresis images showing the results of PCR carried out with the use of a primer that specifically amplifies the marker IB522828 of hybrid progeny lines of "Miyazaki Natsu Haruka" and "08 To-f" (Population A).

FIG. 12-1 shows electrophoresis images showing the results of PCR carried out with the use of a primer that specifically amplifies the marker IB522828 of hybrid progeny lines of "Miyazaki Natsu Haruka" and "Ohkimi" (Population B).

FIG. 12-2 shows electrophoresis images showing the results of PCR carried out with the use of a primer that specifically amplifies the marker IB522828 of hybrid progeny lines of "Miyazaki Natsu Haruka" and "Ohkimi" (Population B).

FIG. 13-1 shows electrophoresis images showing the results of PCR carried out with the use of a primer that specifically amplifies the marker IB522828 of hybrid progeny lines of "Miyazaki Natsu Haruka" and "09s E-b 45e" (Population E).

FIG. 13-2 shows electrophoresis images showing the results of PCR carried out with the use of a primer that specifically amplifies the marker IB522828 of hybrid progeny lines of "Miyazaki Natsu Haruka" and "09s E-b 45e" (Population E).

FIG. 14-1 shows a characteristic diagram summarizing the results of PCR carried out with the use of a primer that specifically amplifies the marker IB522828 of hybrid progeny lines of "Miyazaki Natsu Haruka" and "08 To-f" (Population A), hybrid progeny lines of "Miyazaki Natsu Haruka" and "Ohkimi" (Population B), and hybrid progeny lines of "Miyazaki Natsu Haruka" and "09s E-b 45e" (Population E).

FIG. 14-2 shows a characteristic diagram summarizing the results of PCR carried out with the use of a primer that specifically amplifies the marker IB522828 of hybrid progeny lines of "Miyazaki Natsu Haruka" and "08 To-f" (Population A), hybrid progeny lines of "Miyazaki Natsu Haruka" and "Ohkimi" (Population B), and hybrid progeny lines of "Miyazaki Natsu Haruka" and "09s E-b 45e" (Population E).

EMBODIMENTS FOR CARRYING OUT THE INVENTION

Figure 1:
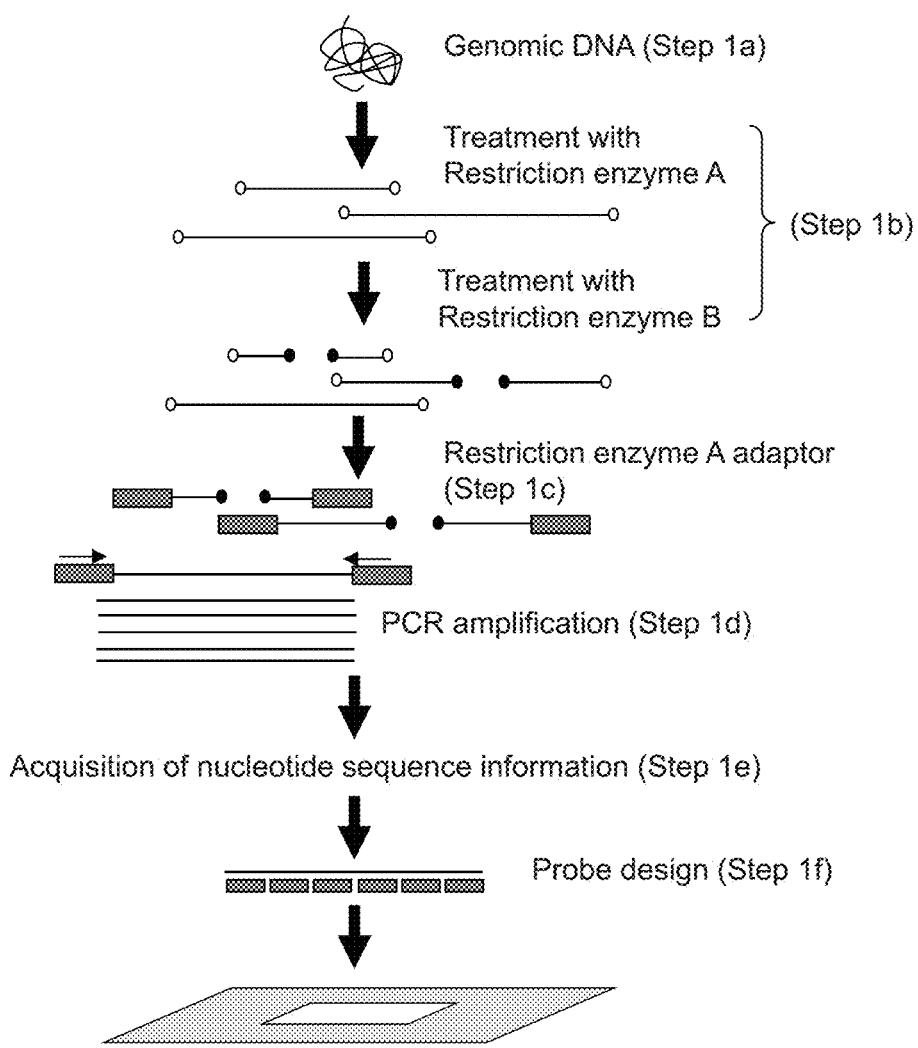
FIG. 1 schematically shows a process for producing a DNA microarray used for obtaining markers in chromosomes of plants of the genus *Fragaria*.

Hereafter, the markers associated with powdery mildew resistance in plants of the genus *Fragaria* of the present invention, the method for using the same, in particular, a method for producing plant lines of the genus *Fragaria* using the markers associated with powdery mildew resistance in plants of the genus *Fragaria* are described.

[Markers Associated with Powdery Mildew Resistance in Plants of the Genus *Fragaria*]

The marker associated with powdery mildew resistance in plants of the genus *Fragaria* according to the present invention is a particular region in the chromosome of a plant of the genus *Fragaria* that makes it possible to identify traits of powdery mildew resistance of a plant of the genus *Fragaria*. By determining the presence or absence of the marker associated with powdery mildew resistance in the plant of the genus *Fragaria* in the progeny lines obtained from existing plants of the genus *Fragaria*, specifically, whether or not a line of interest has powdery mildew resistance can be determined. In the present invention, the term "strawberry powdery mildew" refers to a disease resulting from infection with *Sphaerotheca aphanis* (*Podosphaera aphanis*), leading to development of lesions, as described in Ann. Phytopathol. Soc. Jpn., 64: 121-124, 1998.

In the present invention, strawberry powdery mildews are preferably caused by infection with fungi that are pathogenic for 7 varieties other than "Toyonoka" and "Harunoka" among 9 strawberry varieties; i.e., "Toyonoka," "Nyohou," "Reikou," "Himiko," "Houkou-Wase," "Dana." "Kougyoku," "Harunoka," and "Fukuba" (Race 0, Japanese Journal of Phytopathology Vol. 63, No. 3, p. 226).

The term "a marker associated with powdery mildew resistance in plants of the genus *Fragaria*" refers to a marker linked to traits of a high degree of powdery mildew resistance. When the marker associated with powdery mildew resistance in plants of the genus *Fragaria* is present in a given plant of the genus *Fragaria*, for example, such plant can be determined to have a high degree of powdery mildew resistance. In particular, the marker associated with powdery mildew resistance in plants of the genus *Fragaria* may be considered to be a region linked to a causal gene (or causal genes) of traits such as powdery mildew resistance in plants of the genus *Fragaria*.

The term "plants of the genus *Fragaria*" used herein refers to all plants belonging to the rosaceous genus *Fragaria* (*Fragaria* L.). Specific examples of plants of the genus *Fragaria* include hybrids of general strawberry cultivars, *Fragaria ananassa* (i.e., *Fragaria×ananassa*). Examples of plants of the genus *Fragaria* include plants of *F. virginiana* that are progenitor species of strawberry cultivars and plants of wild species, such as *F. chiloensis. F. vesca, F. iinumae. F. nipponica. F nilgerrensis. F. nubicola. F bucharica. F daltoniana. F. ortentalis, F. cortmbosa, F. moschata*, and *F. iturupensis*. Further. "plants of the genus *Fragaria*" encompass known varieties and lines of strawberry cultivars (*F.×ananassa*). Known varieties and lines of strawberry cultivars are not particularly limited, and any varieties and lines that can be used inside or outside Japan are within the scope thereof. For example, strawberry varieties grown in Japan are not particularly limited. Examples thereof include Toyonoka, Sanchigo, June berry, Nyohou, Pisutoro, Rindamore, Tochiotome, Aisutoro, Tochinomine, Akihime, Benihoppe, Tochihime, Sachinoka, Keikiwase, Sagahonoka, Aiberry, Karen berry, Red pearl, Satsumaotome, Fukuoka S6 (Amaou), Nohime, Hinomine, and Houkou-wase.

The presence or absence of the marker associated with powdery mildew resistance in plants of the genus *Fragaria* can be determined in the above plants of the genus *Fragaria* and progeny lines of the above plants of the genus *Fragaria*. In a progeny line, either the mother plant or father plant may be a plant of the genus *Fragaria* described above. A progeny line may result from sibling crossing or may be a hybrid line. Alternatively, a progeny line may result from so-called back crossing.

It is particularly preferable that the presence or absence of the marker associated with powdery mildew resistance in the plant of the genus *Fragaria* be determined in strawberry cultivars (*F.×ananassa*). In addition, it is preferable that the presence or absence of the marker associated with powdery mildew resistance in the plant of the genus *Fragaria* be determined in improved lines resulting from various varieties and lines of the strawberry cultivars described above. In such a case, powdery mildew resistance of strawberries can be evaluated in produced new varieties. Accordingly, it is preferable that a new variety be derived from a line having powdery mildew resistance in strawberries as either the mother plant or father plant.

The marker associated with powdery mildew resistance in plants of the genus *Fragaria* according to the present invention has been newly identified by QTL (Quantitative Trait Loci) analysis using a genetic linkage map containing 8,218 markers acquired from the strawberry variety "Miyazaki Natsu Haruka" and 8,039 markers acquired from the strawberry line "08 To-f" and data concerning powdery mildew resistance of strawberries. QTL analysis is carried out with the use of the genetic analysis software of QTL Cartographer (Wang S., C. J. Basten and Z.-B. Zeng, 2010, Windows QTL Cartographer 2.5., Department of Statistics, North Carolina State University, Raleigh, N.C.) in accordance with the composite interval mapping (CIM) method.

Specifically, a region exhibiting a LOD score equivalent to or higher than a given threshold (e.g., 2.5) was found in the gene linkage maps by the QTL analysis. A size of a region that is lower than the peak by 1 LOD is approximately 6.8 cM (centimorgan), and this region is included in the 1st linkage group of the strawberry line "08 To-f." The unit "morgan (M)" relatively indicates a distance between genes on the chromosome, and such distance is represented in terms of a percentage of the crossing-over value. In the chromosome of a plant of the genus *Fragaria*, "1 cM" is equivalent to approximately 400 kb. This region has a peak whose LOD score is approximately 7.3. This implies the presence of a causal gene (or causal genes) that improve(s) powdery mildew resistance in plants of the genus *Fragaria* at such peak or in the vicinity thereof.

The 6.8-cM region comprises the 19 types of markers shown in Table 1 in the order shown in Table 1. The marker names indicated in Table 1 were acquired exclusively for the present invention.

TABLE 1

| Seq ID No | Marker name | Nucleotide sequence information |
|---|---|---|
| 1 | IB535110 | GGTGGAATTCATATACCATTTATTTAACAGAAGA GGCTTGTAAGTTATCGATCAATCGATACAAGGTA TAGTGTTGTGATTTTTTCAAGCTAAGATCATCTA ATATCATTCTTTTTTGCAGTTATGCTGGTATGTA AGCCTCTGGGTCTGATCAAATGAGAGTGTATCTA GAACTTTCAACTTGATACTTTGACCATATCGTTT GAGTTTGCCTCATGAAATTTGATTGCAATCTACT ACTGTTTATCTTGCACTCTTTGATGATAGATAAC GCAGCCATGCGTTGAGCACAGACCGAACTACACA TATATGAATCGGAGCCATGGATGCAGCCTTAGTT TCAGGTACTTTGATTATCAATAGTTTCAGCCGCA GTAACAAACAACTATGGCCCTTTCGCATTTTATG AATGTCTCATCTGTTCCTGTCTATACTTGAAATA ATATTATTACATACCAAATACTACTTCGTTGTCC GACGTAAGTATATTAATCTATTTGAACAGCTATG GAGTTCCAATTTTAAATGCATGAAGTAGGAGAAA |

TABLE 1-continued

| Seq ID No | Marker name | Nucleotide sequence information |
|---|---|---|
|  |  | ATTTAGAAACCATGAATTAAGATATTAGAATTCC TACATCATCACCACCCAGAGCCAAGAGAGTTTGG TGGTGTTTCAATTTCAGCCCAAGTTTTCTCTATT CGTCGTCTCCTTCTCCCTCTCCTCCATTATTTCC ATTACATGACAGTTGAAACGCTTTCTCCCGATCG TGTACAATTCATTTTCGATTGAGCATCTTGAGCA GAACTCTGATCACTATTAATTCACTTTCTGATGG CGTTGAGCAGCCAAACTGGGT |
| 2 | IB522828 | TCCAAGACACTTGACGATATCAGACGCAAAGGGT CGTCATATAATCCACTACTGCTGCTTTGACGCCT ACTGCAATAGCATATTCCTATGAATCACCCACCG TGGCAGGCTGGCAGTGTTTTGGCTGTGAATGATG AAGATGATGATGAAATTTGGGTTATGCTCAAGTG GTGCAAACTTTTGAAAGCAACGTGAGCTTTAACG AAGCCCAACCCAAATTAAGTCCTACATTTGAGAG AGACTCTGAGATGAGTGAGATCAGTGCATCATTC TTTGAATCATTCAACAATATCCACTTTCAAAACA AATTTTTCTCTCTTTTGGGTAAACAAACAAGTTT TGAATAGGTTTCCTTCTTCGTAACAAGGACTTG CTACAGAAATGGACCGATAACAACCTGCTGTTCC AGAGGACTCCCCATTCTTCTGTGTAAGGCTTCTG GAGCTCGATGATATCAAAGAAGGGAGGAAGGTAC CTTTGCTTATGTCTCTTTCTTTAATCTTCTCAAA GCTTGTAACTTTGAAAGCTGAAACATGCATTTGC TTCAGTACTGATCTTGTTTTT |
| 3 | IB559302 | CTGGAAGTTCCTGTACATAGGTATATAGTTAGAC TTAGTCACAATGCATAATGGTGGGTTCAAATTAG AGGCAAAACAAGCCATAAACAGATAAAGATACAG CTAAAAACCAAGGCCAAGGGAATAGAAACACAGT AAACATGAAAATTTGAATTGTCCTTCACGGTACA GGGTACAGATTTCAAACTTTTTAGCTGCAAAAAG TTCATAAATCAAGCAGAACCTTTTTCTTTATTGT CCTGCAAGACTTATCTATAAAGGCTTATAATTTC AAGTGTTTGGAAAAAAAAAATGTAAAATAAAAAC AGAACAACAACTGGAATTAACAGAATCATAGAAC TGAAGCAAAGCTCTTTAGTTTCTACTTTCTAGTG AACATGTAAAGATCTCAACTTTCAACTCTCAAGA TTATCAAGCTGTGAAATTAAGTAAACACATGTTC CTAAAAAAAGTGGAAAATGTAAAGGTTTTATCTT TCACGCTAATCAAACAAGATCAGAACTTCTCCAC ACAAAAAAAAACAAGATCAGTA |
| 4 | IB719784 | TTTTTCTTTAGGAGTACGCAAGTCTGCATACCAT GCGACGATCATCTCAAAAAGATAGTAAGTGACCA TGTAAAAATCATTTACCCTCTCAAAATCCCGCCG CCCCCCCACGCCACGATTTCCATTATGTATTCTA TATTTACATATCTCTACAATAGACAAACACTTTC CTCTTTCTTTAGACATGTTACTGAGACCTCACCT ACAAATTTTTCTGACCATCTTAACGCAAAATTTA CAGATCCGGTGATCCGGTAATCCATTTAACCCGA TAAAACATATAAGTGTCGTACATTCCATTTAGAA TCTCTCAATAATAATGCTACATGAGTGTCACTAA TGCTAT |
| 5 | IB508805 | TTCCATATATATACATTAGAATCCTCACTTGCTG ATATTATATGTTTCCCATCTGAAGTGAAAGTGGC AGATCGCAGGTTTGCTGCATTCTTTAATCCTAAA CAAGAGACGAGAGATGAGGTTTAGCAAAAGGAAA TGTCATATATCACATCTAAAATTCACAAACATGT GGCATAAAATTATGCCAAAGGAGTGTAAAATTTG TTTGCAGACAAAGGAATCTCATGAAAAGAGCTTA CGAAATGCACATACCCTTGTATTTTCCAACCACA TTCAAACCATGAAGAATTCTGACTTGTGAATCGG CGCAAGTGACCATTACTTTGTCAGGATCATGAGG GAAATACTGCATTAATAACATAATTTAGAAAAGA AAAAAGAATGGATCCCTAACGAATAGGTAACAAA CACAAGAAACCAAAAGAAGAATACAAAAGTATTA GCTACCTCAAAGCCTGTTATCTTT |
| 6 | IB710861 | AAGAATGAAGAATGTAAAGAGACACTGTCCAGCT TTGAAAAATCTGATCTTGGTCTTAATCAGCGTGG TAATCAAGGCCTTCATGGAATGGTTTGAGCAAGT CGATCAGCTAAAGTATTGTGCGTAAAAATTTTGT GTAGTGTCAAACCGGTGATGTTACTACTGTCAAA CTGGTGATGATACTACTGAGATTGTCAATGATTC |

TABLE 1-continued

| Seq ID No | Marker name | Nucleotide sequence information |
|---|---|---|
| | | AGACGCAGATCATGTTTCTATTGATCCATTTCT TGTTTAACTCTTTATCCAGAGATGACCTTTCGAT CTTCTCATATTTTTCGTAAAAAGAATAAGGTTGC AAATGCTTTAGCTAACCACGGTACGTCATTAACA TAGCTAGTTTGGTAAGATTCACATATTCCTTTTA TTTTGTTATATTGTAGTAGTGACCTTATGAGTCT TTCCCAATTTCGGTTTCTTAGTTTTGTTTCGTTG TTATTTTGTTACGAGAGATTTTGGTCTAATCCTC CTCTCTTGATGTTTCTCTTTTTTCTTTTGTAATG CATAAGAGTGTTCAGAGGTTATTCCTCTCTCACT CATCTTTCAGCCAAAAAAAAAAATTTGCATTAAT TTATTGAAAGTTTTGCTTCATGTGTGT |
| 7 | IB713087 | AGATATATTCGTCGTCAGAGCCACCCACTTCTGCT TGTTGCTGCCTTAACCATGGAGCCTTCTTGTTCA TTCATAGCCTCGTGAACAGAAATGCTGCTATTGG ATTGTTTCATTTACTAATCAGCTCTTCTTTGTCG TGCTCAAACAGTGCACGGGCCCCACATTTCTTCA CCTTCATGTAGCTGCATAAAGGGCGTTTCATGCA TCTGTTGTACCAAGATTCCATCTTTCTCTTCTTT TTGATTTGATTCAGTTGATGTTATTAGAAATACT TGGAGAATTTAATCAATGGGTCTCAGAGTCTATG GATGGTATTTGGTAACAAACGGGTCTGATTGATA TGGTTATCCTTGTTCAAACATTTGGAACCTTAGA ATGTTTCCAACTGATATTGAGTTCAATACTTGCA GGAATTCTAATCTGTGATTTAGTATAAAACTATG AATAAACCAATGGTTTACAGGGAATATACAGCAG GGCAATGGTTT |
| 8 | IB302484 | CTGTAAAAATCAAAGGCAAGCACTTGATGAAAAA GAAGGTTGGTGATTTTGGATTAGATGGGCATCCA TCGTATATAGGCTCTAATATCTTTTGTGGTTGAT TAAACAAATGAGGATCTCTGTAATAAGTGGAGAT TCTTATCATTTCCCACATCTGAGAAACTCTGAAA TAAACAAAAGAAAGAGAAAAAGGCTTTCACGAC AATATGGGTGAAGCATGGGTCCTAACTCCTAAG TTGTAATACCTGTGTTTGTTAAACTACTATACAT AGCAACTCTTGGTGTTGCTCGGTCTAAGG |
| 9 | IB503795 | CTGTAAAAATCAAAAGCAAGCACTTGATGAAAAA GAAGGTTGGTGATTTTGGACGAGATGGACATCCA TCATATATAGGGTCTAATATCTTTTGTGGTTGAT TAAACATATGAGGATCTCTGTAATAAGTGGAGAT TCTTATCATCTCCCACATCTGAGAAACTCAGAAA CAAACAAAAGAAAGAGAAAAAGGCTTTCACGAC AATATGGGTGAAGCATGGGTCCTAAGTTCGTAAT CTCTGTGTTTGTTAAACAACTATATCTATATAT AGTAACTCTTGGTGTTGCTCGGTCTAAGGTTGTA CCAATCAGTGTCTTAGATAGACAAAGTCGGTGGA AGGTGGCAGTAACATATCACAAAGTCTGTTGTGA GGGTGCAACAATATAACGCAACTGTAAACTGTC ACATCAGTTTACAAACTCTACTTACATAAATTTT ATTTAGTGTTCAACGTTCAAACATTACATTCTAT CATATTTCGGTGCATGACATACTTCGCGTTTTGG AC |
| 10 | IB700262 | TGTGGCAAATTACAGACCAAAAGATCTATCTGTC TATCAATGCCGACCTATTCTCATATGGTTTTGGC TTCTATGTGGTGAAGGTTCAACGTTGTTGTTGTT AAGGAAGGTCATCTTGGACTTTTATTTTGTTTCC AAGTTCTATTTATTAATTTCATATGAAAATGATA TATACCTACAGAAGCTAACATTACCCGTGAAATA TTGAACACCCTTTTGATGTCTATACTTCAATAAT GTCTGTCAGATGATTAAGGCAACATATCTTTTAT GGCATCTAAATTGGTTAATTCGATTCGTTTTGAT TTTGTTTTCTCTACTAATTCTGACAATCGAAAAA CCGAACGTGTTAGTCTAGAAATGACGTATTATAA AACACAGGTGTTCCATTTCTAATTTTTCTGCATA ACACCTGCTTTCAGTTGTGATTAGAAAAACATCT TTAAGTTGACATTT |
| 11 | IB515566 | TAACTTCAGGGAGCTAAAGATCATGGGTCGTTTC GACGTCAGATTCGCTTCAACATTAGTTGGTACTT ATCTTCCTAATCTCAAGGTCATGAGCCTGCGGTG TTCGCAGCTGGTTAGGGAAGCTTTGATCACTGTA TTGGACGGGTTACCACAGCTAGAAGTCCTCAATA TAGCACATTGTGTGCTTCTGATTGAACCCCGCG |

TABLE 1-continued

| Seq ID No | Marker name | Nucleotide sequence information |
|---|---|---|
| | | CCGTAATCAGCCTCTCCAAATTGTTGAGGAGGTT GATGAAGTTATTCTTGAGAAGGCTGCTCGGTTAG AGAGATTCATAACGTGCACGCAAATAGACCGGTG CATCCTGTGCCAAAGGGCCAGAAACGACGGGGGG ATTATGAAATGGTATAAATATGAAGAAGGGCTCT GGAAACAAGATGAGGTGAACACTCTTGCTCTTTG ATTCTATTCGAGTGTGTTATGCTTGTAA |
| 12 | IB526892 | CTTCCTATCTGTGACAACAATCCTAACCTTCAAT GAATAGGAGAAGTAGACTATCTCTACCAAATATA CATATATACAGGACTATATGTTTCAAATTATATG TATCCAGATTGGAAAGTTTGCCATCAGATTATT TGCGGTGTAGCATTGTTTGTAAATCATGGAATTG CGTAGCAAACGATAATCGAATCCAACAAGCTAAG ATGATGTCAAATTCTCATCACCCTCCTATGCTCT TGATTCCTGCAAAAGAAGAAGATACATGGAACTT GTACAACATTATGGAAAAAAAAGGTTCTTGATAT GCAAGTCACAGTGCCACCTAACTATAAACCGTTT TCTGGATCCTCAAAGGGATGGTTGATAGCTTTGG ATGAGAATTTTGTAGTAACACTGATAAATCCTTT CTCTAGAGTTAAGGGAAGGAGAGAGAAAGAAAAT TCAATCATTCGGCTTCCTCCTTTGAATCATCAAC AATCGACAATAAGATTACGAGGTGAAGAGTATC |
| 13 | IB504834 | TGTAGCGGAGGGATTGTTTTGTCATTTCAAAACT GAGGGACTTTTTTTTTTATTGAAATTAAACTGAG GGCCTTGCAAGCCGTAGGCGTTGGTACTGGACGG TGCCGTTTTCTTTGATCGAAGTTTTTATGGCAAG GGGTTTAATTGTCCTTTCAAAAATGTTAGAAGTG AAATTTGGGTCAGATGGATGAAGGTTTTCTTGTG TCCATATATACGAGTGTATTATGTTTCGTCGATG TATCGATGATTTATATTAAATTTCAGATTTTAAT TTTGAGACATGAAAAACATTTATAATTTAAGTGA TTTTGTGTTTCTAGCCTTATAGT |
| 14 | IB509379 | AGTGCTATGGAATATGTCTTCGGTTCAACCTTTG TGTGCAAGACTATTAATGCTGCAAAGGAGGTGAG AGGTTGATTATCGTGCTGTAGGCTGATTATATAG TATTGTCCTTTTAAACACTTGTAATCTAAGCAGG AAAGCGGCATGACCCAATCTGGTTCTCTATGAAT GTTTCCTAGGTTGCTTTTAACAGGGAAGTTCGTA CCCTAGTGTCACTCTTGAAGGTGATATCTTCCAG CCCAGTGGTCTTTTGACTGGTGGAAGCCGCAAGT AAGCCACTGTTCTTTTTCCTCCAGTTTAGATTTC ATGCTTTACCCCCTTCCTCTTGAGTATATCTGTT GTTAGCTCTCTCTGACTAATTTTCCATACTTGTG TTGTCCTTATCATTTATCAATTCAAAGTACATAT ACTTCTAGCCAGTTTTCCTTCTAAAGCAAAAATT TCCTGTCACAGGGGTGGGGGAGATCTGTTAAG |
| 15 | IB518714 | TAGGTGATATTTGACGTGCAAGTGTCCAAAATAA TCTCATAAGGCCTAACTCCCCCATCGTCACAATT TGACCATCAAACTATCTCCAGCGCTACCTGTTGT CGGCACCCTCTACCGACGTTATTTCACAACCATT TTAATTAACGTTCGATTTGTTTCAGTGAAAAACA AACAGTTGGTAGTAAAAGATCATGGTAAAAAGCA GACTGCGTGGTGGGTGGATGTACACAACGCGGA GTAGAACGCTTAAAGTTTTTCACACCACTAATAA TATATTATACATATTATATAATACAAAACCTGTA ATTATAAATATACATAATATATTCTTAAGAAAAC TTTGCGAGGTAAAAGTGGTGGCGGCAAGGCACTT TGAGTGATTAGAATTGGGAGGTTTTGGTGGTGGA TGACACTGAATATAGTGCCGGATGCTTGCCGGGT |
| 16 | IB522595 | AAATTGTTTCCATATGATACGGTTCAACATGACA CTTACATAGTTACATTAGCATAGAAGTCAACATT GCCTCTCTTTCTCACAACTGATCAAACTCTACCT GATCAGGCAGGCCAATCAAGAGAGGATTTGACTG CATTTCAGCAAAATAAGCACATATGCAACACCCT ATGCACATATACAAGAGTGGCACATTGCCTTCA CATTTGCCTAAAAGTACATAAAACTAACAGAAGC ATCCATGAAAGCTCCATGGCAACCACTTCTCAAC TCCATTGCCTAGTTAAACAATGTAGATCATAATT AAAACAGATATTTGAGGAGCAGGAAA |
| 17 | IB712150 | CAAACCGGGTTTAGACTTGCTACGATCAAGTTGT TCTTCAATCTGCTCTGCCATTCTCCCTACATCAT |

TABLE 1-continued

| Seq ID No | Marker name | Nucleotide sequence information |
|---|---|---|
| | | AGACACCCGGAAAGTGTGAGGGCTAATGTGATTG<br>CCAACAATATAATTGATGCTTTGAATAGAGGGGT<br>GAACTTGGATGACAAGGAGAGTAAGGATAGTGGT<br>GTTTCGCATTTGACTGATTTGAATTGGGAGGTTT<br>TGGTGGTGGATGACACTGAATATAGTGCCGGATG<br>CTTGCCGGGTGGGAAGATTGTGGTCTGCTCAGGG<br>CTGCTCAAGCATTATTTTAGTGATGCGGAGATAG<br>CTATGGTAATTGCTCATGAGGTACGATGACTAGT<br>TGTGTAGTGTTTCTGTTCAAAGTGCTAAAACAAT<br>GTGGGCTGCTAACTTCTCCTCTGTCTTGTGATTG<br>CAAGCTAGGTTGGGCATACTGTGGCTCGACACCA<br>AGCTGAGTTAGTCACAAAGTTCCTGTGGC |
| 18 | IB722030 | TGTAGCGGAGGGATTGTTTTGTCATTTCAAAACT<br>GAGGGACTTTTTTTTTATTGAAATTAAACTGAGG<br>GCCTTGCAAGCCGTAGGCGTTGGTACTGGACGGT<br>GCCGTTTTCTTTGATCGAAGTTTTTATGGCAAGG<br>GGTTTAATTGTCCTTTCAAAAATGTTAGAAGTGA<br>AATTTGGGTCAGATGGATGAAGGTTTTCTTCTGT<br>CCATATATACGAGTGTATTATGTTTCGTCGATGT<br>ATCGATGATTTATATTAAATTTCAGATTTTAATT<br>TTGAGACATGAAAAACATTTATAATTTAAGTGAT<br>TTTGTGTTTCTAGCGTTATAGTGCGTATGAATGA<br>GACACAACGTACAAAAAAGTTGAGATAAGAAAAT<br>GACCCATAAATTATTTTGGTTTTAATTTATGTAA<br>GCGATATTTTTAGGTTGGTTGATTATGAATTTAT<br>GTACATTAAAATTCAAAATATTTTTTGGCACAT<br>TAGATTGTAAACTTGAATCAATAGTACTTGACGT<br>CGTTAGCATGATTGAATTGTCAAATGTTGTATAT<br>TTTGAAAGGTAAAAAGGTACCTCTCTTCACTTCA<br>TCTTTTTTGTCTCTAAACCACACCAAGACTTTGC<br>GCAAAGCCCTCCATCTTTACATCAAATGGTGATA<br>TTCTAAGTCGCATACCAAAACCCCGATCTCCAAG<br>ACTCGACTCCCAAATCTGGAGATGGAGGTGACAA<br>CACGACTAGAATCACAGCTTTGGTACTATCATGA<br>CAATAAGTTGAACAACTTTGGTCGTCTGGGTATG<br>CT |
| 19 | IB726514 | GAAAACCCCATCATCTTTAATCCTTTGCTGAGGG<br>GAAGCACAAGGGCTCAACAGCTATAACATTGAGC<br>AACTACTATAGTTAGTCCTGTGATTGGAAGTGCC<br>AAGGGTCTTCAAAATAACCGGGGCAATCTATGGC<br>CATGGTTCTATGTATATACATAATCCTCTATCCT<br>AGTTATGCTACCAAATATGTTCTGAGACATAATC<br>GTTCTTCTGTTGCTCGGAACAATGCAGAAAACTT<br>AAAATAGTAAAAGTGTTGTTATAGAATCTCCTCA<br>AAATTTTAGACCATTTTAGGGAAATTCTATCAGT<br>GTTTCAATCGTTAGACACTTCAAGTCCTAGTATA<br>CTAATCCAAAAGCCTCACTACAAAAATACATGAA<br>GACATTTACATGCGACCATACTAGCCTTCCTCTA<br>TCAGAACGAACCAACACTAAGAAGAGCATCATAG<br>GATACATAATCCTCTATCCGTAAACAAATGACAA<br>TCAGAAGAAACA |

Specifically, the marker associated with powdery mildew resistance in plants of the genus *Fragaria* according to the present invention is a continuous nucleic acid region sandwiched between the nucleotide sequence as shown in SEQ ID NO: 1 and the nucleotide sequence as shown in SEQ ID NO: 19 in the chromosome of the plant of the genus *Fragaria*. The peak in the 6.8-cM region is located in a region sandwiched between the marker comprising the nucleotide sequence as shown in SEQ ID NO: 1 (IB535110) and the marker comprising the nucleotide sequence as shown in SEQ ID NO: 7 (IB713087).

A continuous nucleic acid region in the 6.8-cM region shown in Table 1 can be used as the marker associated with powdery mildew resistance in plants of the genus *Fragaria*. The term "nucleic acid region" used herein refers to a region comprising a nucleotide sequence having 95% or less, preferably 90% or less, more preferably 80% or less, and most preferably 70% or less identity to the other region in the chromosome of the plant of the genus *Fragaria*. As long as the degree of identity between the nucleic acid region as the marker associated with powdery mildew resistance in plants of the genus *Fragaria* and the other region is within the range described above, such nucleic acid region can be specifically detected in accordance with a conventional technique. The degree of identity can be determined using, for example, BLAST with the default parameters.

A nucleic acid region serving as the marker associated with powdery mildew resistance in plants of the genus *Fragaria* can comprise at least 8, preferably 15 or more, more preferably 20 or more, and most preferably 30 nucleotides. As long as the number of nucleotides constituting the nucleic acid region as the marker associated with powdery mildew resistance in plants of the genus *Fragaria* is within such range, such nucleic acid region can be specifically detected in accordance with a conventional technique.

In particular, the marker associated with powdery mildew resistance in plants of the genus *Fragaria* is preferably selected from a region sandwiched between the nucleotide sequence as shown in SEQ ID NO: 1 and the nucleotide sequence as shown in SEQ ID NO: 7 among the 19 types of markers included in the 6.8-cM region because the peak is located in the region sandwiched between the nucleotide sequence as shown in SEQ ID NO: 1 and the nucleotide sequence as shown in SEQ ID NO: 7.

The marker associated with powdery mildew resistance in plants of the genus *Fragaria* can be a nucleic acid region including a single type of marker selected from among the 19 types of markers shown in Table 1. For example, use of a nucleic acid region including a marker comprising the nucleotide sequence as shown in SEQ ID NO: 1 (IB535110), which is located in a position nearest to the peak, as the marker associated with powdery mildew resistance in plants of the genus *Fragaria* is preferable. In such a case, the nucleotide sequence of the nucleic acid region including the marker can be identified by a method of flank sequence analysis, such as inverse PCR using primers designed based on the nucleotide sequence of the marker.

Alternatively, a plurality of regions may be selected from a nucleic acid region sandwiched between the nucleotide sequence as shown in SEQ ID NO: 1 and the nucleotide sequence as shown in SEQ ID NO: 19 in the chromosome of the plant of the genus *Fragaria* as the marker associated with powdery mildew resistance in the plant of the genus *Fragaria*.

In addition, any of the above 19 types of markers can be directly used as markers associated with powdery mildew resistance in plants of the genus *Fragaria*. Specifically, one or more regions selected from the 19 regions comprising the nucleotide sequences as shown in SEQ ID NOs: 1 to 19 can be used as markers associated with powdery mildew resistance in plants of the genus *Fragaria*. For example, use of a marker comprising the nucleotide sequence as shown in SEQ ID NO: 1 (IB535110), which is located in a position nearest to the peak, as a marker associated with powdery mildew resistance in plants of the genus *Fragaria* is preferable. Alternatively, a region sandwiched between the marker comprising the nucleotide sequence as shown in SEQ ID NO: 2 (IB522828) and the marker comprising the nucleotide sequence as shown in SEQ ID NO: 3 (IB559302) can be used as a marker associated with powdery mildew resistance in plants of the genus *Fragaria*, for example.

[Identification of Marker in Plants of the Genus *Fragaria*]

In the present invention, as described above, the markers associated with powdery mildew resistance in plants of the genus *Fragaria* were identified from among the 8,218 markers acquired from the strawberry variety "Miyazaki Natsu Haruka" and the 8,039 markers acquired from the strawberry line "08 To-f." Such 8,218 markers and 8,039 markers are described below. These markers can be identified with the use of a DNA microarray in accordance with the methods disclosed in JP 2011-120558 A or WO 2011/074510.

Specifically, probes used for the DNA microarray are designed in the manner shown in FIG. 1. That is, genomic DNA is first extracted from "Miyazaki Natsu Haruka" or "08 To-f" (Step 1a). Subsequently, the extracted genomic DNA is digested with one or more restriction enzymes (Step 1b). In an embodiment shown in FIG. 1, two types of restriction enzymes, Restriction enzyme A and Restriction enzyme B, are used in that order to digest genomic DNA. Restriction enzymes are not particularly limited, and examples of restriction enzymes that can be used include PstI, EcoRI, HindIII, BstNI, HpaII, and HaeIII. Restriction enzymes can be adequately selected by taking, for example, the frequency of recognition sequence appearance into consideration, so as to yield a genomic DNA fragment with 20 to 10,000 nucleotides upon complete digestion of genomic DNA. When a plurality of restriction enzymes are used, it is preferable that the genomic DNA fragment comprise 200 to 6,000 nucleotides after all the restriction enzymes are used. When a plurality of restriction enzymes are used, in addition, the order in which restriction enzymes are subjected to treatment is not particularly limited. Under common treatment conditions (e.g., a solution composition or temperature), a plurality of restriction enzymes may be used in the same reaction system. While Restriction enzyme A and Restriction enzyme B are successively used in that order so as to digest genomic DNA in an embodiment shown in FIG. 1, specifically. Restriction enzyme A and Restriction enzyme B may be simultaneously used in the same reaction system to digest genomic DNA. Alternatively, Restriction enzyme B and Restriction enzyme A may be successively used in that order, so as to digest genomic DNA. In addition, 3 or more restriction enzymes may be used.

Subsequently, adaptors are bound to the genomic DNA fragment treated with restriction enzymes (Step 1c). The adaptors used herein are not particularly limited, provided that such adaptors can be bound to the both ends of the genomic DNA fragment obtained through the treatment with restriction enzymes. An example of an adaptor that can be used is an adaptor comprising a single strand that is complementary to a protruding end (a sticky end) formed at both ends of the genomic DNA fragment obtained through the treatment with restriction enzymes and having a primer-binding sequence to which a primer used at the time of amplification can hybridize (details are described below). Alternatively, an adaptor comprising a single strand complementary to the protruding end (a sticky end) and having a restriction enzyme recognition site to be incorporated into a vector at the time of cloning can be used.

When genomic DNA is digested with a plurality of restriction enzymes, a plurality of adaptors corresponding to relevant restriction enzymes can be used. Specifically, a plurality of adaptors each comprising a single strand complementary to any of a plurality of types of protruding ends resulting from digestion of genomic DNA with a plurality of types of restriction enzymes can be used. In such a case, a plurality of adaptors corresponding to a plurality of restriction enzymes may have common primer-binding sequences enabling hybridization of common primers. Alternatively, such adaptors may have different primer-binding sequences, so that different primers can hybridize thereto.

When genomic DNA is digested with a plurality of restriction enzymes, in addition, an adaptor corresponding to a restriction enzyme selected from among the plurality of restriction enzymes used or adaptors corresponding to a subset of restriction enzymes selected from among the plurality of restriction enzymes used can be prepared.

Subsequently, a genomic DNA fragment comprising adaptors bound to both ends thereof is amplified (Step 1d). When adaptors comprising primer-binding sequences are used, primers that can hybridize to such primer-binding sequences may be used, so that the genomic DNA fragment can be amplified. Alternatively, a genomic DNA fragment comprising adaptors added thereto may be cloned into a vector using the adaptor sequences, and primers that can hybridize to particular regions in such vector may be used, so as to amplify the genomic DNA fragment. An example of an amplification reaction of the genomic DNA fragment with the use of primers is PCR.

When genomic DNA is digested with a plurality of restriction enzymes and a plurality of adaptors corresponding to relevant restriction enzymes are ligated to the genomic DNA fragments, adaptors would be ligated to all genomic DNA fragments resulting from the treatment with the plurality of restriction enzymes. In such a case, primer-binding sequences contained in the adaptors may be used to perform a nucleic acid amplification reaction. Thus, all resulting genomic DNA fragments can be amplified.

When genomic DNA is digested with a plurality of restriction enzymes and an adaptor corresponding to a restriction enzyme selected from among the plurality of restriction enzymes used or adaptors corresponding to a subset of restriction enzymes selected from among the plurality of restriction enzymes used are ligated to the genomic DNA fragments, alternatively, the genomic DNA fragments comprising the recognition sequences for the selected restriction enzymes at both ends thereof can be selectively amplified among the resulting genomic DNA fragments.

Subsequently, nucleotide sequences of the amplified genomic DNA fragments are determined (Step 1e), one or more regions of a nucleotide length shorter than that of the genomic DNA fragment and corresponding to at least a part of the genomic DNA fragment are identified, and the one or more identified regions are designed as probes in strawberry cultivars (Step 1f). A method for determining nucleotide sequences of genomic DNA fragments is not particularly limited. For example, a conventional technique involving the use of a DNA sequencer in accordance with the Sanger's method can be employed. A region to be designed herein is of, for example, a 20- to 100-nucleotide length, preferably a 30- to 90-nucleotide length, and more preferably a 50- to 75-nucleotide length, as described above.

As described above, many probes are designed using genomic DNAs extracted from strawberry cultivars, and oligonucleotides comprising target nucleotide sequences are synthesized on a support based on the nucleotide sequences of the designed probes. Thus, a DNA microarray can be produced. With the use of the DNA microarray produced as described above, the 8,218 markers and the 8,039 markers including the 19 types of markers associated with powdery mildew resistance in plants of the genus *Fragaria* as shown in SEQ ID NOs: 1 to 19 can be identified.

More specifically, the present inventors obtained the signal data with the use of the DNA microarray concerning 8,215 markers obtained from the strawberry variety "Miyazaki Natsu Haruka," the strawberry line "08 To-f," and hybrid progeny lines thereof (147 lines). They then obtained the genotype data from the obtained signal data, and, on the basis of the obtained genotype data, they obtained the positional information for markers in the chromosomes in accordance with a genetic distance calculation formula (Kosambi) using genetic map production software (AntMap, Iwata, H., Ninomiya, S., 2006, AntMap: Constructing genetic linkage maps using an ant colony optimization algorithm. Breed Sci., 56: 371-378). On the basis of the positional information for the obtained markers, in addition, a genetic map datasheet was prepared using the Mapmaker/EXP ver. 3.0 (A Whitehead Institute for Biomedical Research Technical Report, Third Edition, January, 1993). As a result, the 8,218 markers and the 8,039 markers including the 19 types of markers associated with powdery mildew resistance in plants of the genus *Fragaria* as shown in SEQ ID NOs: 1 to 19 are identified.

[Use of Markers Associated with Powdery Mildew Resistance in Plants of the Genus *Fragaria*]

With the use of the markers associated with powdery mildew resistance in plants of the genus *Fragaria*, whether or not plants of the genus *Fragaria* whose powdery mildew resistance remains unknown (e.g., progeny lines) have powdery mildew resistance can be determined. The use of markers associated with powdery mildew resistance in plants of the genus *Fragaria* includes an embodiment of the use of a method that specifically amplifies a nucleic acid fragment comprising the markers and an embodiment of the use of a DNA microarray comprising probes corresponding to the markers.

The method that specifically amplifies a nucleic acid fragment comprising markers associated with powdery mildew resistance in plants of the genus *Fragaria* is a method of so-called nucleic acid amplification. Examples of methods of nucleic acid amplification include a method involving the use of a primer designed so as to specifically amplify a target nucleic acid fragment and a method of specifically amplifying a target nucleic acid fragment without the use of a primer.

A primer that specifically amplifies a target nucleic acid fragment is an oligonucleotide that can amplify a nucleic acid fragment comprising a marker associated with powdery mildew resistance in plants of the genus *Fragaria* as defined above by a method of nucleic acid amplification. Methods of nucleic acid amplification involving the use of primers are not particularly limited, and any method may be employed, provided that a nucleic acid fragment is amplified. A representative example is a polymerase chain reaction (PCR). Examples of other methods include, but are not limited to, conventional techniques, such as rolling circle amplification (RCA), cycling probe technology (CPT), isothermal and chimeric-primer-initiated amplification of nucleic acids (ICAN), loop-mediated isothermal amplification of DNA (LAMP), strand displacement amplification (SDA), nucleic-acid-sequence-based amplification (NASBA), and transcription-mediated amplification (TMA).

When PCR is selected from among such nucleic acid amplification reactions, for example, a pair of primers are designed so as to sandwich markers associated with powdery mildew resistance in plants of the genus *Fragaria* in the chromosome of the plant of the genus *Fragaria*. When the LAMP method is employed, 4 types of primers are designed so as to sandwich the markers associated with powdery mildew resistance in plants of the genus *Fragaria* in the chromosome of plants of the genus *Fragaria*.

A method of nucleic acid amplification to be performed without the use of a primer is not particularly limited, and an example thereof is a method of ligase chain reaction (LCR). When the method of LCR is employed, a plurality of oligonucleotides that hybridize to nucleic acid fragments containing the markers associated with powdery mildew resistance in plants of the genus *Fragaria* are designed.

When the markers associated with powdery mildew resistance in plants of the genus *Fragaria* are present in the target plants of the genus *Fragaria*, as described above, nucleic acid fragments containing the markers can be obtained as amplification products according to methods of nucleic acid amplification. When a nucleic acid fragment of interest is amplified via a method of nucleic acid amplification using, as a template, the chromosome extracted from the target plant of the genus *Fragaria*, in other words, the target plant of the genus *Fragaria* can be determined to have powdery mildew resistance.

Methods for detecting an amplified nucleic acid fragment are not particularly limited. Examples thereof include a method in which a solution resulting after the amplification reaction is subjected to agarose electrophoresis, and a fluorescent intercalator, such as ethidium bromide or SYBR green, is allowed to bind thereto, so as to observe specific fluorescence, a method in which a fluorescent intercalator is added to a solution used for nucleic acid amplification, so as to detect fluorescence after the amplification reaction, and a method in which nucleic acid amplification is carried out with the use of a fluorescence-labeled primer, so as to detect fluorescence after the amplification reaction.

When the markers associated with powdery mildew resistance in plants of the genus *Fragaria* are detected via a method of nucleic acid amplification, an amplified fragment containing such markers can contain, for example, 30 to 10.000, preferably 50 to 5,000, and more preferably 70 to 2,000 nucleotides, although the number of nucleotides would vary depending on the principle of the method of nucleic acid amplification.

When evaluating the powdery mildew resistance of plants of the genus *Fragaria*, a plurality of markers associated with powdery mildew resistance in plants of the genus *Fragaria* may be detected. Specifically, a plurality of regions selected from nucleic acid regions sandwiched between the nucleotide sequence as shown in SEQ ID NO: 1 and the nucleotide sequence as shown in SEQ ID NO: 19 in the chromosome of plants of the genus *Fragaria* may be designated as the markers associated with powdery mildew resistance in plants of the genus *Fragaria*, and the plurality of markers associated with powdery mildew resistance in plants of the genus *Fragaria* may be detected. For example, a plurality of regions selected from among 19 regions consisting of nucleotide sequences as shown in SEQ ID NOs: 1 to 19 may be designated as the markers associated with powdery mildew resistance in plants of the genus *Fragaria*, and the plurality of regions may be detected.

For example, the region comprising the nucleotide sequence as shown in SEQ ID NO: 1 (IB535110) and the region comprising the nucleotide sequence as shown in SEQ ID NO: 2 (IB522828) may be designated as the markers associated with powdery mildew resistance in plants of the genus *Fragaria*, and these regions may be subjected to nucleic acid amplification, so as to determine the presence or absence of the markers associated with powdery mildew resistance in plants of the genus *Fragaria*. Alternatively, a region sandwiched between the region comprising the nucleotide sequence as shown in SEQ ID NO: 2 (IB522828) and the region comprising the nucleotide sequence as shown in SEQ ID NO: 3 (IB559302) may be designated as the marker associated with powdery mildew resistance in plants of the genus *Fragaria*, and the region may be subjected to nucleic acid amplification, so as to determine the presence or absence of the marker associated with powdery mildew resistance in plants of the genus *Fragaria*.

According to an embodiment in which a DNA microarray comprising probes corresponding to the markers associated with powdery mildew resistance in plants of the genus *Fragaria* is used, the probes are oligonucleotides that can hybridize specifically to the markers associated with powdery mildew resistance in plants of the genus *Fragaria* as defined above under stringent conditions. Such an oligonucleotide can be designed as, for example, a partial region comprising 10, 15, 20, 25, 30, 35, 40, 45, 50, or more continuous nucleotides in the nucleotide sequence of the marker associated with powdery mildew resistance in plants of the genus *Fragaria* as defined above or a complementary strand thereof or the entire region of the nucleotide sequence. The DNA microarray comprising probes may be, for example, a microarray comprising a planar substrate of glass or silicone as a carrier, a bead array comprising microbeads as carriers, or a three-dimensional microarray comprising probes immobilized on the inner wall of a hollow fiber.

With the use of the DNA microarray thus produced, whether or not a plant of the genus *Fragaria* whose phenotypic characteristics with regard to powdery mildew resistance remain unknown (e.g., a progeny line) exhibits a phenotype indicating excellent powdery mildew resistance can be determined. Alternatively, the marker associated with powdery mildew resistance in plants of the genus *Fragaria* may be detected in accordance with a conventional technique, and whether or not the target plants of the genus *Fragaria* have excellent powdery mildew resistance may be determined by a method other than the method involving the use of a DNA microarray. An example of a method other than the method involving the use of a DNA microarray that can be employed is so-called FISH (fluorescence in situ hybridization) involving the use of the probes described above.

Figure 2:
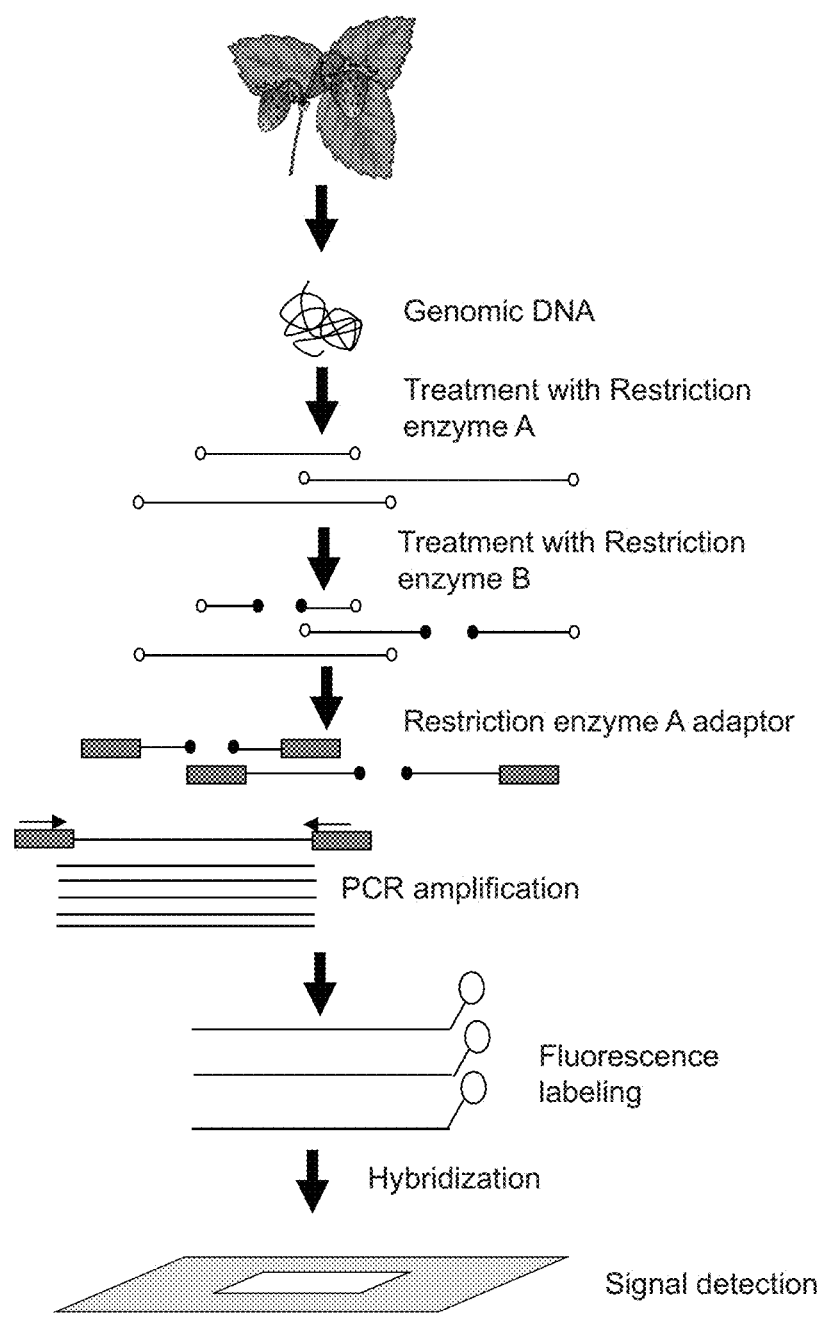
FIG. 2 schematically shows a step of signal detection using a DNA microarray.

A method involving the use of a DNA microarray is described in greater detail. As shown in FIG. 2, genomic DNA is first extracted from a target plant of the genus *Fragaria*. A target plant of the genus *Fragaria* is a plant of the genus *Fragaria* with unknown phenotypic characteristics in terms of powdery mildew resistance (e.g., a progeny line) and/or a parent plant of the genus *Fragaria* used when producing a progeny line, which is to be evaluated as to excellent powdery mildew resistance.

Subsequently, the extracted genomic DNA is digested with the restriction enzyme used when preparing the DNA microarray described in the [Identification of markers in plants of the genus *Fragaria*] section above, so as to prepare a plurality of genomic DNA fragments. The resulting genomic DNA fragments are then ligated to adaptors used when preparing the DNA microarray. The genomic DNA fragments comprising adaptors added to the both ends are then amplified using the primers used when preparing the DNA microarray. Thus, the genomic DNA fragments derived from the target plant of the genus *Fragaria* corresponding to the genomic DNA fragment amplified in Step Id when preparing a DNA microarray can be amplified.

In this step, among the genomic DNA fragments comprising adaptors added thereto, specific genomic DNA fragments may be selectively amplified. When a plurality of adaptors corresponding to the plurality of restriction enzymes are used, for example, genomic DNA fragments comprising specific adaptors added thereto can be selectively amplified. When genomic DNA is digested with a plurality of restriction enzymes, adaptors are selectively added to the genomic DNA fragments having protruding ends corresponding to specific restriction enzymes among the resulting genomic DNA fragments. Thus, genomic DNA fragments comprising the adaptors added thereto can be selectively amplified. By selectively amplifying specific genomic DNA fragments, as described above, these fragments can be concentrated.

Subsequently, the amplified genomic DNA fragments are labeled. Any conventional material may be used as a label. Examples of labels that can be used include fluorescent molecules, pigment molecules, and radioactive molecules. This step can be omitted with the use of a labeled nucleotide in the step of genomic DNA fragment amplification. That is, a genomic DNA fragment is amplified with the use of a labeled nucleotide in the above step, so that the amplified DNA fragment is labeled.

Subsequently, a labeled genomic DNA fragment is brought into contact with a DNA microarray under given conditions, so as to allow a probe immobilized on a DNA microarray to hybridize to the labeled genomic DNA fragment. It is preferable that hybridization be carried out under highly stringent conditions. Under highly stringent conditions, whether or not the marker associated with powdery mildew resistance in plants of the genus *Fragaria* is present in the target plant of the genus *Fragaria* can be determined with higher accuracy. Stringent conditions can be adjusted based on reaction temperature and salt concentration. Specifically, higher stringency can be realized by increasing temperature or decreasing salt concentration. When a probe comprising 50 to 75 nucleotides is used, for example, hybridization can be carried out at 40° C. to 44° C. in 0.2% SDS and 6×SSC, so that higher stringency can be realized.

Hybridization between a probe and a labeled genomic DNA fragment can be detected based on a label. After the hybridization reaction between the labeled genomic DNA fragment and the probes, specifically, unreacted genomic DNA fragments or the like are washed, and a label bound to the genomic DNA fragment that had specifically hybridized to the probes are then observed. In the case that the label is a fluorescent material, for example, the fluorescent wavelength thereof is detected. When a label is a pigment molecule, the pigment wavelength thereof is detected. More specifically, apparatuses such as fluorescence detectors or image analyzers used for conventional DNA microarray analysis can be used.

By the method involving nucleic acid amplification or the method involving the use of a DNA microarray, as described above, whether or not the target plant of the genus *Fragaria* has the marker associated with powdery mildew resistance in plants of the genus *Fragaria* can be determined. As described above, a marker associated with powdery mildew resistance in plants of the genus *Fragaria* is linked to traits of excellent powdery mildew resistance. If a marker associated with powdery mildew resistance in plants of the genus *Fragaria* is present, accordingly, the target plant can be determined to be of a line or variety excellent in powdery mildew resistance.

According to the method described above, in particular, it is not necessary to have the target plant of the genus *Fragaria* grow to the extent that the target plant can actually be subjected to the test as to powdery mildew resistance. For example, seeds of progeny lines or young seedlings germinated from such seeds can be used. With the use of the markers associated with powdery mildew resistance in plants of the genus *Fragaria*, accordingly, cost of the field for growing the target plant of the genus *Fragaria* and cost for growing the plant can be reduced to a significant extent. Also, the use of markers associated with powdery mildew resistance in plants of the genus *Fragaria* eliminates the need to actually infect plants with microorganisms causing powdery mildew (i.e., *Sphaerotheca aphanis*). Thus, expenditures required for equipment such as a large-scale greenhouse for an exclusive purpose, a field for an exclusive purpose, or a facility isolated from the outside can be reduced.

When producing new varieties of the plants of the genus *Fragaria*, it is particularly preferable that several tens of thousands of types of hybrid species be first produced via crossing and evaluation take place prior to or instead of seedling selection with the use of the markers associated with powdery mildew resistance in plants of the genus *Fragaria*. Thus, the number of plants to be grown in the actual field can be reduced to a significant extent, and the labor and expenditures required for the production of new varieties of plants of the genus *Fragaria* can be reduced to a significant extent.

When producing new varieties of plants of the genus *Fragaria*, alternatively, the presence or absence of the markers associated with powdery mildew resistance in plants of the genus *Fragaria* in the parent varieties to be used for crossing is first evaluated, and parent varieties with excellent powdery mildew resistance can be selected. By producing progeny lines with the preferential use of parent varieties with excellent powdery mildew resistance, progeny lines with excellent powdery mildew resistance can develop at high frequency. Thus, the number of plants necessary to cultivate in order to produce superior lines can be reduced to a significant extent, and the labor and expenditures required for the production of new plant varieties of the genus *Fragaria* can be reduced to a significant extent.

Examples

Hereafter, the present invention is described in greater detail with reference to the examples, although the technical scope of the present invention is not limited to these examples.
1. Preparation of DNA Microarray Probe
(1) Materials
The strawberry varieties: "Miyazaki Natsu Haruka" and "08 To-f," were used.
(2) Treatment with Restriction Enzyme
Genomic DNA was extracted from these strawberry varieties using the Dneasy Plant Mini Kit (Qiagen). The extracted genomic DNA (150 ng) was treated with the PstI restriction enzyme (5 units, NEB) at 37° C. for 1 hour.
(3) Ligation of Adaptors
The PstI sequence adaptors (5'-CACGATGGATCCAGTGCA-3' (SEQ ID NO: 20) and 5'-CTGGATCCATCGTGCA-3' (SEQ ID NO: 21)) and T4 DNA ligase (200 units, NEB) were added to the genomic DNA fragment (150 ng) treated in (2) above, and the resultant was subjected to ligation at 16° C. for 1 hour, 55° C. for 20 minutes, and then 37° C. for 30 minutes. Subsequently, the BstNI restriction enzyme (6 units, NEB) was added to the treated sample, and the sample was then treated at 60° C. for 1 hour.
(4) Amplification by PCR
The PstI sequence adaptor recognition primer (5'-GATGGATCCAGTGCAG-3' (SEQ ID NO: 22)) and Taq polymerase (1.25 units, PrimeSTAR, Takara Bio Inc.) were added to the sample treated with the BstNI restriction enzyme (15 ng) obtained in (3) above, and the DNA fragment was amplified by PCR (30 cycles of 98° C. for 10 seconds, 55° C. for 15 seconds, and 72° C. for 1 minute, and treatment at 72° C. for 3 minutes, followed by storage at 4° C.).
(5) Acquisition of Genome Sequence
The nucleotide sequence information of the genomic DNA fragment amplified by PCR in (4) above was determined using Hiseq 2000 (Miseq, Illumina).
(6) Design of Probes and Preparation of DNA Microarray
On the basis of the genome sequence information acquired in (5) above, 50 to 60 bp probes were designed. On the basis of the nucleotide sequence information of the designed probes, a DNA microarray comprising these probes was produced.
2. Acquisition of Signal Data
(1) Materials
The strawberry varieties: "Miyazaki Natsu Haruka" and "08 To-f," and 147 hybrid progeny lines thereof were used.
(2) Treatment with Restriction Enzyme
Genomic DNA was extracted from these strawberry varieties and the hybrid progeny lines using the Dneasy Plant Mini Kit (Qiagen). The extracted genomic DNA (150 ng) was treated with the PstI restriction enzyme (6 units, NEB) at 37° C. for 1 hour.
(3) Ligation of Adaptors
The PstI sequence adaptors (5'-CACGATGGATCCAGTGCA-3' (SEQ ID NO: 20) and 5'-CTGGATCCATCGTGCA-3' (SEQ ID NO: 21)) and T4 DNA ligase (200 units, NEB) were added to the genomic DNA fragment (150 ng) treated in (2) above, and the resultant was subjected to ligation at 16° C. for 1 hour, 55° C. for 20 minutes, and then 37° C. for 30 minutes. Subsequently, the BstNI restriction enzyme (6 units, NEB) was added to the treated sample, and the sample was then treated at 60° C. for 1 hour.
(4) Amplification by PCR
The PstI sequence adaptor recognition primer (5'-GATGGATCCAGTGCAG-3' (SEQ ID NO: 22)) and Taq polymerase (1.25 units, PrimeSTAR, Takara Bio Inc.) were added to the sample treated with the BstNI restriction enzyme (15 ng) obtained in (3) above, and the genomic DNA fragment was amplified by PCR (30 cycles of 98° C. for 10 seconds, 55° C. for 15 seconds, and 72° C. for 1 minute, and treatment at 72° C. for 3 minutes, followed by storage at 4° C.).
(5) Labeling
The DNA fragment amplified in (4) above was purified through a column (Qiagen), and a labeled sample was then prepared using a NimbleGen One-Color DNA Labeling kit (Roche Diagnostics K.K.) in accordance with the NimbleGen Arrays User's Guide.
(6) Hybridization and Signal Detection
Hybridization was carried out by the array CGH (aCGH) method involving the use of the Agilent in-situ oligo DNA microarray kit using the labeled sample obtained in (5) above and the DNA microarray prepared in 1. above. Signals from the samples were detected.
3. Identification of QTL Associated with Powdery Mildew Resistance of Strawberries and Selection of Selection Markers
(1) Preparation of Gene Map Data Sheet
From the signal data of the 147 hybrid progeny lines of "Miyazaki Natsu Haruka" and "08 To-f," the genotype data of "Miyazaki Natsu Haruka"-type 8,218 markers and "08 To-f"-type 8,039 markers were obtained. On the basis of the genotype data, the gene mapping data of the markers were obtained in accordance with the genetic distance calculation formula (Kosambi) using the genetic map production software (AntMap, Iwata. H., Ninomiya, S., 2006, AntMap:

Constructing genetic linkage maps using an ant colony optimization algorithm. Breed Sci. 56: 371-378).

(2) Acquisition of Phenotype Data of Strawberry Powdery Mildew

Figure 3:
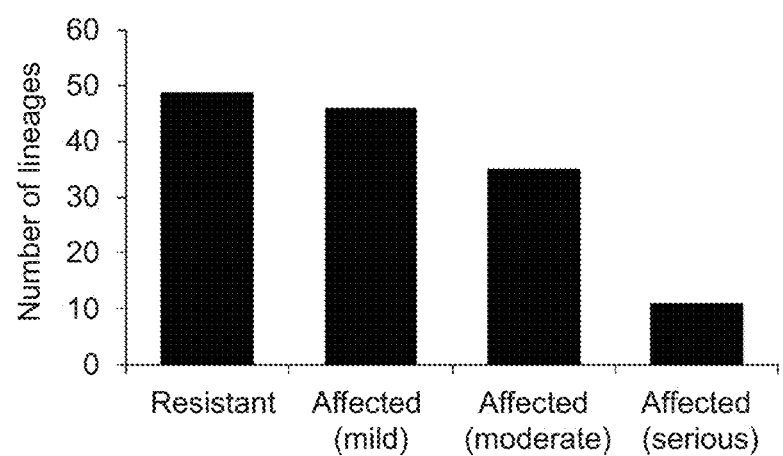
FIG. 3 shows a characteristic diagram showing the results of inspection concerning the onset and extent of strawberry powdery mildew of hybrid progeny lines of the "Miyazaki Natsu Haruka" and "08 To-f."

Seeds of the 147 hybrid progeny lines of "Miyazaki Natsu Haruka" and "08 To-f" were grown to seedlings in a greenhouse, the resulting seedlings were transplanted in an outdoor field in spring on the following year, and the onset and extent of strawberry powdery mildew was inspected in summer (FIG. 3). Affected plants were evaluated in terms of the severity at 3 different stages: mild, moderate, and severe.

In this example, the plants were naturally infected with powdery mildew fungi indigenous in the soil of Morioka, Iwate, Japan.

(3) Analysis of Quantitative Trait Loci (QTL)

On the basis of the genetic map data obtained in (1) above and the results of strawberry powdery mildew test obtained in (2) above (i.e., the onset and extent of powdery mildew). QTL analysis was carried out by the composite interval mapping (CIM) method with the use of the genetic analysis software (QTL Cartographer, Wang S., C. J. Basten, and Z.-B. Zeng, 2010, Windows QTL Cartographer 2.5. Department of Statistics, North Carolina State University, Raleigh, N.C.). The LOD threshold was designated to be 2.5. As a result, the presence of the gene associated with powdery mildew resistance of strawberries (LOD value: 7.3) was detected in a region between the IB535110 marker and the IB726514 marker in the 1st linkage group of "08 To-f" (Table 2, FIG. 4).

(4) Selection of Selection Marker

Figure 4:
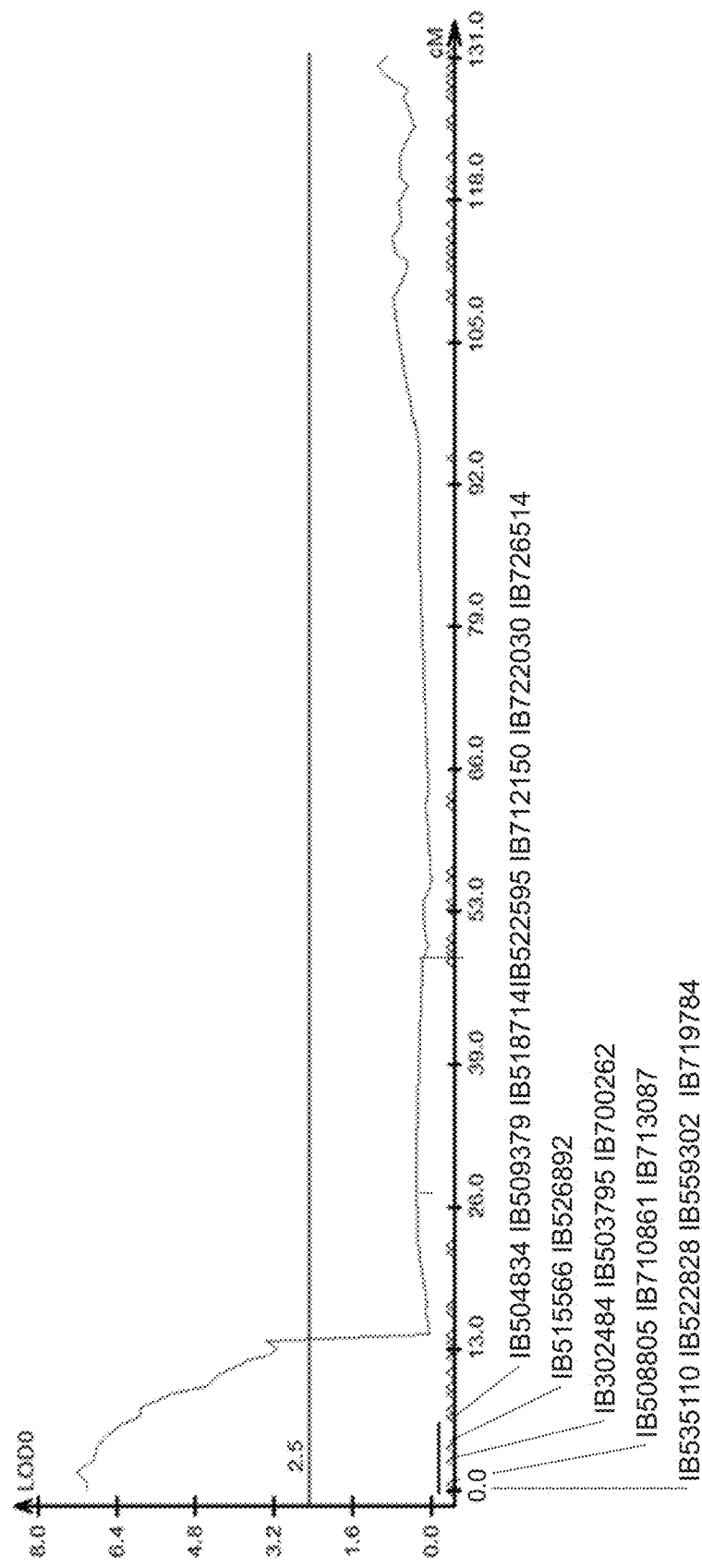
FIG. 4 shows a characteristic diagram showing the results of QTL analysis concerning powdery mildew resistance (the 1st linkage group of "08 To-f").
Figures 2, 11:
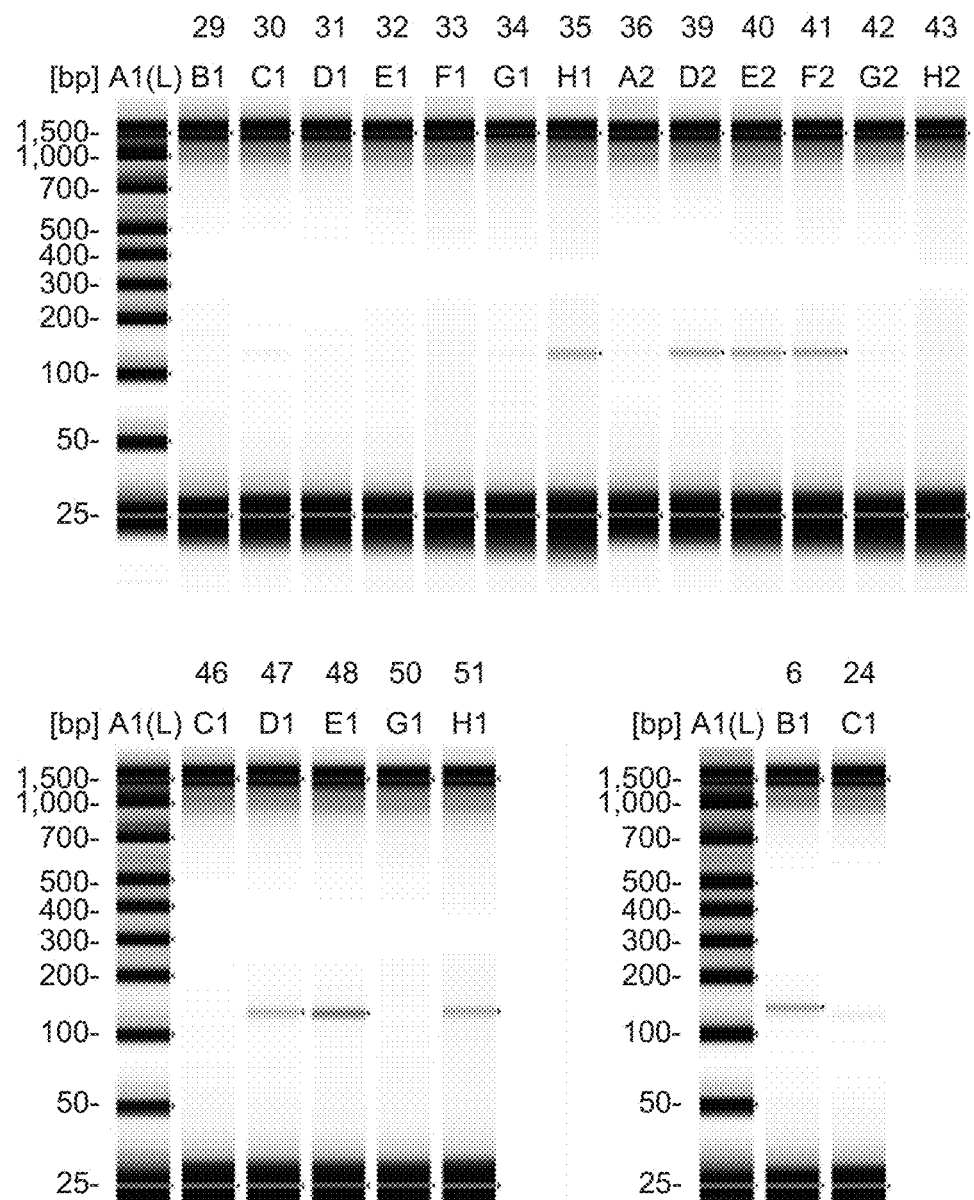
Figures 3, 11:
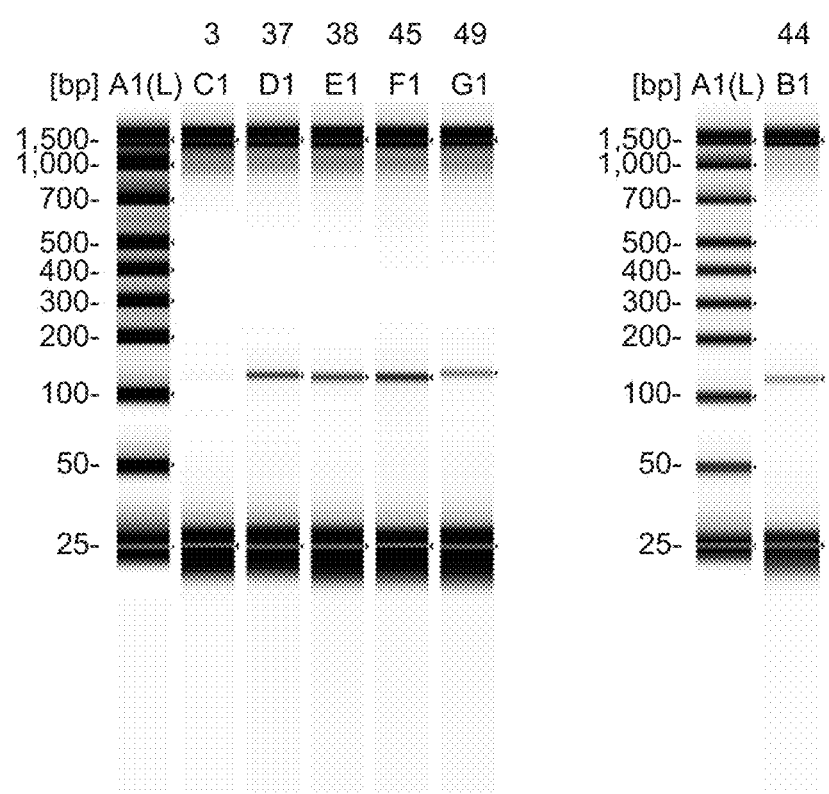
Figures 1, 12:
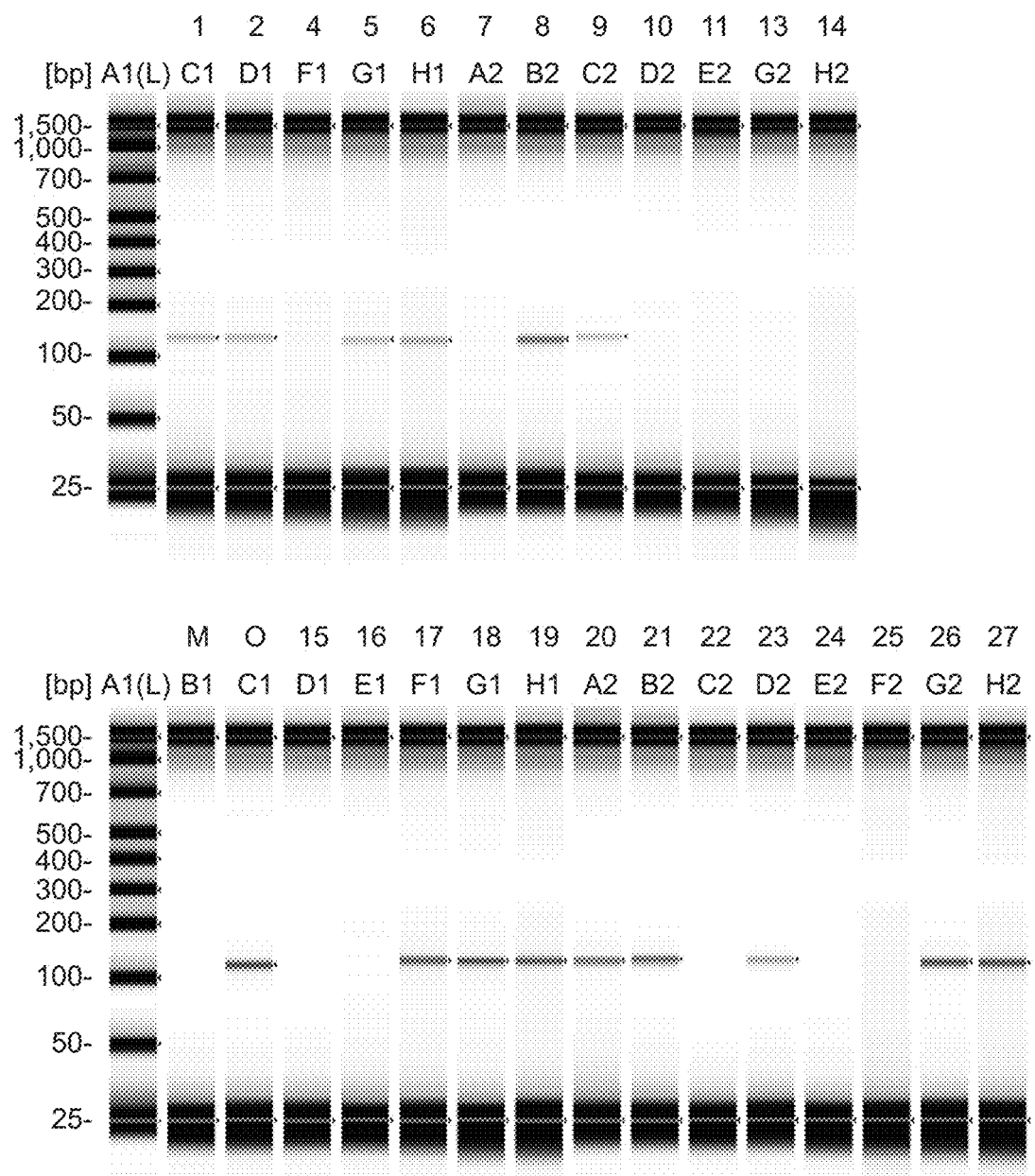
Figures 2, 13:
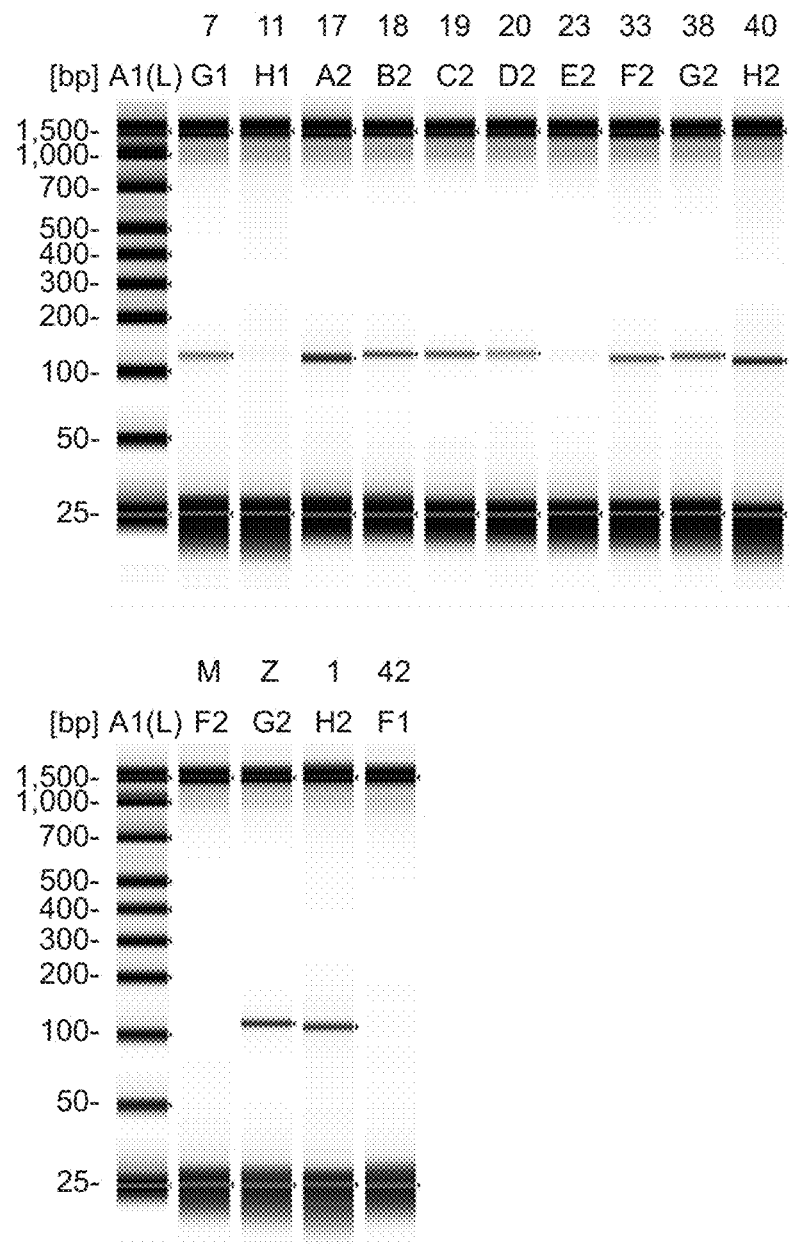

Markers in the vicinity of the region of the strawberry powdery mildew resistant gene in a region from 0 cM to 6.83 cM of the 1st linkage group were selected as selection markers (FIG. 4, Table 1).

Haruka" and "08 To-f" were grown to seedlings in a greenhouse (50 lines, hereafter referred to as "Population A"), the resulting seedlings were transplanted in an outdoor field in autumn, and the onset and extent of strawberry powdery mildew was inspected in summer on the following year. In addition, hybrid progeny lines of "Miyazaki Natsu Haruka" and "Ohkimi" (42 lines, hereafter referred to as "Population B") and hybrid progeny lines of "Miyazaki Natsu Haruka" and "09s E-b 45e" (42 lines, hereafter referred to as "Population E") were grown to seedling, transplanted, and then inspected in terms of the onset and extent of powdery mildew in the same manner (FIGS. 5-1 and 5-2).

(2) Extraction of Genomic DNA

Separately, genomic DNAs were extracted from the strawberry varieties: "Miyazaki Natsu Haruka" and "08 To-f," and Population A, respectively, using the Dneasy Plant Mini Kit (Qiagen).

(3) Treatment with Restriction Enzyme and Ligation of Adaptor

The extracted genomic DNA (150 ng) was treated with the PstI restriction enzyme (5 units, NEB) at 37° C. for 1 hour, the PstI sequence adaptors (5'-CACGATGGATCCA-GTGCA-3' (SEQ ID NO: 20) and 5'-CTGGATCCATCGT-GCA-3' (SEQ ID NO: 21)) and T4 DNA ligase (200 units, NEB) were added to the sample treated with PstI, and the resultant was subjected to the reaction at 16° C. for 1 hour, 55° C. for 20 minutes, and then 37° C. for 30 minutes. The BstNI restriction enzyme (6 units, NEB) was added to the treated sample, and the sample was then treated at 60° C. for 1 hour.

(4) Amplification of DNA Fragment

The PstI sequence adaptor recognition primer (5'-GATG-GATCCAGTGCAG-3' (SEQ ID NO: 22)) and Taq poly-

TABLE 2

QTL concerning strawberry powdery mildew resistance

| Variety | Linkage group | Position (cM) | Range (cM) | Flanking markers | LOD value | Effect* | Contribution rate (%) |
|---|---|---|---|---|---|---|---|
| 08 To-f | 1 | 0.0 | 6.8 | IB535110-IB726514 | 7.3 | −0.8 | 15.7 |

*Extent of powdery mildews (0: none; 1: mild; 2: moderate; 3: severe)

In Table 2, the column of the effects indicates an influence of the QTL on the onset and extent of powdery mildews (0: none; 1: mild; 2: moderate; 3: severe). If the numeral value indicating the effects is a negative value, specifically, an extent of powdery mildew is lowered, and such QTL is linked to a trait that improves the powdery mildew resistance.

As shown in FIG. 4, a marker located in the vicinity of such peak is inherited in linkage with a causal gene (or causal genes) capable of improving the powdery mildew resistance. This indicates that such marker may be used as the marker associated with powdery mildew resistance in plants of the genus *Fragaria*. Specifically, the 19 types of markers shown in FIG. 4 were found to be usable as the markers associated with powdery mildew resistance in plants of the genus *Fragaria*.

4. Selection of Unknown Line (1) Acquisition of Phenotype Data of Strawberry Powdery Mildew Separately from the lines described in "3. (2) Acquisition of phenotype data of strawberry powdery mildew" above, seeds of the hybrid progeny lines of "Miyazaki Natsu merase (1.25 units, PrimeSTAR, Takara Bio Inc.) were added to the sample treated with the BstNI restriction enzyme (15 ng) obtained in (3) above, and the DNA fragment was amplified by PCR (30 cycles of 98° C. for 10 seconds, 55° C. for 15 seconds, and 72° C. for 1 minute, and treatment at 72° C. for 3 minutes, followed by storage at 4° C.).

(5) Labeling

The DNA fragment amplified in (4) above was purified through a column (Qiagen), and a labeled sample was then prepared using a NimbleGen One-Color DNA Labeling kit (Roche Diagnostics K.K.) in accordance with the Nimble-Gen Arrays User's Guide.

(6) Hybridization and Signal Detection

Hybridization was carried out by the array CGH (aCGH) method involving the use of the Agilent in-situ oligo DNA microarray kit using the fluorescence-labeled sample obtained in (6) above and the array prepared in 1. above. Signals from the samples were detected.

(7) Test of Selection Marker

In Population A, the markers in the vicinity of the region of the strawberry powdery mildew resistant gene were selected (Table 1), the array signal values regarding the selection markers and the phenotypes of Population A were compared, and the degrees of consistency were found to be 90.0% to 98.0% (FIGS. 6-1 to 6-5). In FIGS. 6-1 to 6-5, high array signal values were underlined. The results indicate that the use of the markers shown in Table 1 enables selection of lines that are excellent and lines that are poor in terms of powdery mildew resistance.

5. Selection and Test Using PCR Base Marker 1

(1) Extraction of Genomic DNA

Genomic DNAs were extracted from the strawberry varieties: "Miyazaki Natsu Haruka," "08 To-f," "Ohkimi," and "09s E-b 45e," Population A (51 lines), Population B (42 lines), and Population E (42 lines), using the Dneasy Plant Mini Kit (Qiagen).

(2) Preparation of Primer

With the use of PCR primer analytic software (Primer 3), primers that recognize the sequences of IB535110 were prepared on the basis of the sequence information thereof (SEQ ID NO: 1) (35110_v1F: ACACATATATGAATCG-GAGCCA (SEQ ID NO: 23); 35110_v1R: GCTCAAGAT-GCTCAATCGAA (SEQ ID NO: 24)).

(3) Amplification by PCR and Test of Selection Marker

The above pair of the primers (35110_v1F and 35110_v1R) and Taq polymerase (1.25 units, Tks Gflex DNA Polymerase, Takara Bio Inc.) were added to the genomic DNAs (15 ng each) of the hybrid progeny lines: Population A. Population B, and Population E, and the genomic DNAs were amplified by PCR (30 cycles of 94° C. for 1 minute, 98° C. for 10 seconds, 60° C. for 15 seconds, and 68° C. for 30 seconds, followed by storage at 4° C.). The PCR-amplified DNA fragment was confirmed using the TapeStation D1000 (Agilent). The results attained for Population A, Population B, and Population E are shown in FIGS. 7-1 and 7-2, FIGS. 8-1 and 8-2, and FIGS. 9-1 and 9-2, respectively. In FIGS. 7-1 to 9-2, lane M represents "Miyazaki Natsu Haruka" and lane Z represents "08 To-f." These results are summarized in FIGS. 10-1 and 10-2. In FIGS. 10-1 and 10-2, underlines are provided when phenotypes are not consistent with the results attained with the use of PCR markers. As shown in FIGS. 7-1 to 10-2, the degree of consistency between band patterns and phenotypes is very high (i.e., 98.5%) and the method of nucleic acid amplification involving the use of primers that specifically amplify IB535110 enables selection of lines that are excellent and lines that are poor in terms of powdery mildew resistance.

6. Selection and Test Using PCR Base Marker 2

(1) Extraction of Genomic DNA

Genomic DNAs were extracted from the strawberry varieties: "Miyazaki Natsu Haruka," "08 To-f." "Ohkimi," and "09s E-b 45e," Population A (51 lines), Population B (42 lines), and Population E (42 lines), using the Dneasy Plant Mini Kit (Qiagen).

(2) Preparation of Primer

With the use of PCR primer analytic software (Primer 3), primers that recognize the sequences of IB533828 were prepared on the basis of the sequence information thereof (SEQ ID NO: 2) (22828_v6F: CTTTGACGCCTACTGCA-TIA (SEQ ID NO: 25) and 22828_v6R: GGTTGGGCT-TCGTTAAATCT (SEQ ID NO: 26)).

(3) Amplification by PCR and Test of Selection Marker

The above pair of the primers (22828_v6F and 22828_v6R) and Taq polymerase (1.25 units, Tks Gflex DNA Polymerase, Takara Bio Inc.) were added to the genomic DNAs (15 ng each) of the hybrid progeny lines: Population A, Population B, and Population E, and the genomic DNAs were amplified by PCR (30 cycles of 94° C. for 1 minute, 98° C. for 10 seconds, 60° C. for 15 seconds, and 68° C. for 30 seconds, followed by storage at 4° C.). The PCR-amplified DNA fragment was confirmed using the TapeStation D1000 (Agilent). The results attained for Population A, Population B. and Population E are shown in FIGS. 11-1 to 11-3, FIGS. 12-1 and 12-2, and FIGS. 13-1 and 13-2, respectively. In FIGS. 11-1 to 13-2, lane M represents "Miyazaki Natsu Haruka," lane Z represents "08 To-f," and lane O represents "Ohkimi." These results are summarized in FIGS. 14-1 and 14-2. In FIGS. 14-1 and 14-2, underlines are provided when phenotypes are not consistent with the results attained with the use of PCR markers. As shown in FIGS. 11-1 to 14-2, the degree of consistency between band patterns and phenotypes is very high (i.e., 98.5%) and the method of nucleic acid amplification involving the use of primers that specifically amplify IB522828 enables selection of lines that are excellent and lines that are poor in terms of powdery mildew resistance.

All publications, patents, and patent applications cited herein are incorporated herein by reference in their entirety.

The invention claimed is:

1. A method for producing a plant line of the genus *Fragaria* having powdery mildew resistance comprising:
   (a) extracting genomic DNA from a progeny plant whose at least one parent is a plant of the genus *Fragaria* or a genomic DNA from a plant of the genus *Fragaria*;
   (b) determining by nucleic acid assay the quantity of a nucleic acid marker associated with powdery mildew resistance in the genomic DNA of the plant, wherein the marker comprises at least 20 continuous nucleotides of SEQ ID NO: 1;
   (c) detecting a plant with an increased quantity of the marker compared to the quantity detected in affected plants;
   (d) selecting the plant as a plant having powdery mildew resistance; and
   (e) using the selected plant as a parent plant for crossing to thereby produce a plant line of the genus *Fragaria* having powdery mildew resistance.

2. The method for producing a plant line of the genus *Fragaria* according to claim 1, wherein the determining comprises conducting a nucleic acid amplification reaction using a primer that specifically amplifies the marker associated with powdery mildew resistance in the plant of the genus *Fragaria* to determine the presence of the marker associated with powdery mildew resistance in the plant of the genus *Fragaria*.

3. The method for producing a plant line of the genus *Fragaria* according to claim 1, wherein the determining involves the use of a DNA chip comprising a probe corresponding to the marker associated with powdery mildew resistance in the plant of the genus *Fragaria*.

4. The method for producing a plant line of the genus *Fragaria* according to claim 1, wherein the progeny plant is a seed or seedling and the genomic DNA is extracted from the seed or seedling.

* * * * *

SEQUENCE LISTING

```
<160> NUMBER OF SEQ ID NOS: 26

<210> SEQ ID NO 1
<211> LENGTH: 803
<212> TYPE: DNA
<213> ORGANISM: Fragaria x ananassa

<400> SEQUENCE: 1
ggtggaattc ataccatt tatttaacag aagaggcttg taagttatcg atcaatcgat      60
acaaggtata gtgttgtgat tttttcaagc taagatcatc taatatcatt cttttttgca    120
gttatgctgg tatgtaagcc tctgggtctg atcaaatgag agtgtatcta gaactttcaa    180
cttgatactt tgaccatatc gtttgagttt gcctcatgaa atttgattgc aatctactac    240
tgtttatctt gcactctttg atgatagata acgcagccat gcgttgagca cagaccgaac    300
tacacatata tgaatcggag ccatggatgc agccttagtt tcaggtactt tgattatcaa    360
tagtttcagc cgcagtaaca aacaactatg gcccttttcgc attttatgaa tgtctcatct    420
```

```
gttcctgtct atacttgaaa taatattatt acataccaaa tactacttcg ttgtccgacg    480
taagtatatt aatctatttg aacagctatg gagttccaat tttaaatgca tgaagtagga    540
gaaaatttag aaccatgaa ttaagatatt agaattccta catcatcacc acccagagcc    600
aagagagttt ggtggtgttt caatttcagc ccaagttttc tctattcgtc gtctccttct    660
ccctctcctc cattatttcc attacatgac agttgaaacg ctttctcccg atcgtgtaca    720
attcattttc gattgagcat cttgagcaga actctgatca ctattaattc actttctgat    780
ggcgttgagc agccaaactg ggt                                            803

<210> SEQ ID NO 2
<211> LENGTH: 565
<212> TYPE: DNA
<213> ORGANISM: Fragaria x ananassa

<400> SEQUENCE: 2
tccaagacac ttgacgatat cagacgcaaa gggtcgtcat ataatccact actgctgctt     60
tgacgcctac tgcaatagca tattcctatg aatcacccac cgtggcaggc tggcagtgtt    120
ttggctgtga atgatgaaga tgatgatgaa atttgggtta tgctcaagtg gtgcaaactt    180
ttgaaagcaa cgtgagcttt aacgaagccc aacccaaatt aagtcctaca tttgagagag    240
actctgagat gagtgagatc agtgcatcat tctttgaatc attcaacaat atccactttc    300
aaaacaaatt tttctctctt tgggtaaac aaacaagttt tgaataggtt tccttcttct    360
gtaacaagga cttgctacag aaatggaccg ataacaacct gctgttccag aggactcccc    420
attcttctgt gtaaggcttc tggagctcga tgatatcaaa aagggagga aggtaccttt    480 gcttatgtct ctttctttaa tcttctcaaa gcttgtaact ttgaaagctg aaacatgcat    540
ttgcttcagt actgatcttg ttttt                                         565

<210> SEQ ID NO 3
<211> LENGTH: 532
<212> TYPE: DNA
<213> ORGANISM: Fragaria x ananassa

<400> SEQUENCE: 3
ctggaagttc ctgtacatag gtatatagtt agacttagtc acaatgcata atggtgggtt     60
caaattagag gcaaaacaag ccataaacag ataaagatac agctaaaaac caaggccaag    120
ggaatagaaa cacagtaaac atgaaaattt gaattgtcct tcacggtaca gggtacagat    180
ttcaaacttt ttagctgcaa aaagttcata aatcaagcag aacctttttc tttattgtcc    240
tgcaagactt atctataaag gcttataatt tcaagtgttt ggaaaaaaaa aatgtaaaat    300
aaaaacagaa caacaactgg aattaacaga atcatagaac tgaagcaaag ctctttagtt    360
tctactttct agtgaacatg taaagatctc aactttcaac tctcaagatt atcaagctgt    420
gaaattaagt aaacacatgt tcctaaaaaa agtggaaaat gtaaaggttt tatctttcac    480
gctaatcaaa caagatcaga acttctccac acaaaaaaaa acaagatcag ta           532

<210> SEQ ID NO 4
<211> LENGTH: 346
<212> TYPE: DNA
<213> ORGANISM: Fragaria x ananassa

<400> SEQUENCE: 4 tttttctttta ggagtacgca agtctgcata ccatgcgacg atcatctcaa aaagatagta     60
agtgaccatg taaaaatcat ttaccctctc aaaatcccgc cgccccccca cgccacgatt    120
```

```
tccattatgt attctatatt tacatatctc tacaatagac aaacactttc ctctttcttt    180
agacatgtta ctgagacctc acctacaaat ttttctgacc atcttaacgc aaaatttaca    240
gatccggtga tccggtaatc catttaaccc gataaaacat ataagtgtcg tacattccat    300
ttagaatctc tcaataataa tgctacatga gtgtcactaa tgctat                   346
```

<210> SEQ ID NO 5
<211> LENGTH: 466
<212> TYPE: DNA
<213> ORGANISM: Fragaria x ananassa

<400> SEQUENCE: 5

```
ttccatatat atacattaga atcctcactt gctgatatta tatgtttccc atctgaagtg     60
aaagtggcag atcgcaggtt tgctgcattc tttaatccta acaagagac gagagatgag    120 gtttagcaaa aggaaatgtc atatatcaca tctaaaattc acaaacatgt ggcataaaat    180
tatgccaaag gagtgtaaaa tttgtttgca gacaaaggaa tctcatgaaa agagcttacg    240
aaatgcacat acccttgtat tttccaacca cattcaaacc atgaagaatt ctgacttgtg    300
aatcggcgca agtgaccatt actttgtcag gatcatgagg gaaatactgc attaataaca    360
taatttagaa aagaaaaaag aatggatccc taacgaatag gtaacaaaca caagaaacca    420
aaagaagaat acaaaagtat tagctacctc aaagcctgtt atcttt                   466
```

<210> SEQ ID NO 6
<211> LENGTH: 605
<212> TYPE: DNA
<213> ORGANISM: Fragaria x ananassa

<400> SEQUENCE: 6

```
aagaatgaag aatgtaaaga gacactgtcc agctttgaaa aatctgatct tggtcttaat     60
cagcgtggta atcaaggcct tcatggaatg gtttgagcaa gtcgatcagc taaagtattg    120
tgcgtaaaaa ttttgtgtag tgtcaaaccg gtgatgttac tactgtcaaa ctggtgatga    180
tactactgag attgtcaatg attcagacgc agatcatgtt ttctattgat ccatttcttg    240
tttaactctt tatccagaga tgaccttccg atcttctcat attttctgta aaaagaataa    300
ggttgcaaat gctttagcta accacggtac gtcattaaca tagctagttt ggtaagattc    360
acatattcct tttattttgt tatattgtag tagtgacctt atgagtcttt cccaatttcg    420
gtttcttagt tttgtttcgt tgttattttg ttacgagaga ttttggtcta atcctcctct    480
cttgatgttt ctctttttc ttttgtaatg cataagagtg ttcagaggtt attcctctct    540
cactcatctt tcagccaaaa aaaaaaattt gcattaattt attgaaagtt ttgcttcatg    600
tgtgt                                                               605
```

<210> SEQ ID NO 7
<211> LENGTH: 487
<212> TYPE: DNA
<213> ORGANISM: Fragaria x ananassa

<400> SEQUENCE: 7

```
agatatattc gtcgtcagag ccaccacttc tgcttgttgc tgccttaacc atggagcctt     60
cttgttcatt catagcctcg tgaacagaaa tgctgctatt ggattgtttc atttactaat    120
cagctcttct ttgtcgtgct caaacagtgc acgggcccca catttcttca ccttcatgta    180
gctgcataaa gggcgtttca tgcatctgtt gtaccaagat tccatctttc tcttcttttt    240
gatttgattc agttgatgtt attagaaata cttggagaat ttaatcaatg ggtctcagag    300
```

```
tctatggatg gtatttggta acaaacgggt ctgattgata tggttatcct tgttcaaaca      360
tttggaacct tagaatgttt ccaactgata ttgagttcaa tacttgcagg aattctaatc      420
tgtgatttag tataaaacta tgaataaacc aatggtttac agggaatata cagcagggca      480
atggttt                                                                487

<210> SEQ ID NO 8
<211> LENGTH: 301
<212> TYPE: DNA
<213> ORGANISM: Fragaria x ananassa

<400> SEQUENCE: 8
ctgtaaaaat caaaggcaag cacttgatga aaagaaggt tggtgatttt ggattagatg        60
ggcatccatc gtatataggc tctaatatct tttgtggttg attaaacaaa tgaggatctc      120
tgtaataagt ggagattctt atcatttccc acatctgaga aactctgaaa taaacaaaaa      180
gaaagagaaa aaggctttca cgacaatatg ggtgaagcat ggggtcctaa ctcctaagtt      240
gtaatacctg tgtttgttaa actactatac atagcaactc ttggtgttgc tcggtctaag      300
g                                                                       301

<210> SEQ ID NO 9
<211> LENGTH: 512
<212> TYPE: DNA
<213> ORGANISM: Fragaria x ananassa

<400> SEQUENCE: 9
ctgtaaaaat caaagcaag cacttgatga aaagaaggt tggtgatttt ggacgagatg         60
gacatccatc atatataggc tctaatatct tttgtggttg attaaacata tgaggatctc      120
tgtaataagt ggagattctt atcatctccc acatctgaga aactcagaaa caaacaaaaa      180
gaaagagaaa aaggctttca cgacaatatg ggtgaagcat gggtcctaag ttcgtaatct      240
ctgtgtttgt taaacaacta taatctatat atagtaactc ttggtgttgc tcggtctaag      300
gttgtaccaa tcagtgtctt agatagacaa agtcggtgga aggtggcagt aacatatcac      360
aaagtctgtt gtgagggttg caacaatata acgcaactgt aaactgtcac atcagtttac      420
aaactctact tacataaatt ttatttagtg ttcaacgttc aaacattaca ttctatcata      480
tttcggtgca tgacatactt cgcgttttgg ac                                    512

<210> SEQ ID NO 10
<211> LENGTH: 456
<212> TYPE: DNA
<213> ORGANISM: Fragaria x ananassa

<400> SEQUENCE: 10
tgtggcaaat tacagaccaa agatctatc tgtctatcaa tgccgaccta ttctcatatg        60
gttttggctt ctatgtggtg aaggttcaac gttgttgttg ttaaggaagg tcatcttgga      120
cttttatttt gtttccaagt tctatttatt aatttcatat gaaaatgata tatacctaca      180
gaagctaaca ttacccgtga aatattgaac accctttga tgtctatact tcaataatgt       240
ctgtcagatg attaaggcaa actatctttt atggcatcta aattggttaa ttcgattcgt      300
tttgattttg tttctctac taattctgac aatcgaaaaa ccgaacgtgt tagtctagaa       360
atgacgtatt ataaaacaca ggtgttccat ttctaatttt tctgcataac acctgctttc      420
agttgtgatt agaaaaacat ctttaagttg acattt                                456
```

<210> SEQ ID NO 11
<211> LENGTH: 436
<212> TYPE: DNA
<213> ORGANISM: Fragaria x ananassa

<400> SEQUENCE: 11

```
taacttcagg gagctaaaga tcatgggtcg tttcgacgtc agattcgctt caacattagt      60
tggtacttat cttcctaatc tcaaggtcat gagcctgcgg tgttcgcagc tggttaggga     120
agctttgatc actgtattgg acgggttacc acagctagaa gtcctcaata tagcacattg     180
tgtgcttctg attgaacccc cgcgccgtaa tcagcctctc caaattgttg aggagcttga     240
tgaagttatt cttgagaagg ctgctcggtt agagagattc ataacgtgca cgcaaataga     300
ccggtgcatc ctgtgccaaa gggccagaaa cgacgggggg attatgaaat ggtataaata     360
tgaagaaggg ctctggaaac aagatgaggt gaacactctt gctctttgat tctattcgag     420
tgtgttatgc ttgtaa                                                     436
```

<210> SEQ ID NO 12
<211> LENGTH: 509
<212> TYPE: DNA
<213> ORGANISM: Fragaria x ananassa

<400> SEQUENCE: 12

```
cttcctatct gtgacaacaa tcctaacctt caatgaatag gagaagtaga ctatctctac      60
caaatataca tatatacagg actatatgtt tcaaattata tgtatccaga ttggaaaagt     120
ttgccatcag attatttgcg gtgtagcatt gtttgtaaat catggaattg cgtagcaaac     180
gataatcgaa tccaacaagc taagatgatg tcaaattctc atcaccctcc tatgctcttg     240
attcctgcaa aagaagaaga tacatggaac ttgtacaaca ttatggaaaa aaaaggttct     300
tgatatgcaa gtcacagtgc cacctaacta taaacggttt tctggatcct caaagggatg     360
gttgatagct ttggatgaga attttgtagt aacactgata aatcctttct ctagagttaa     420
gggaaggaga gagaaagaaa attcaatcat tcggcttcct cctttgaatc atcaacaatc     480
gacaataaga ttacgaggtg aagagtatc                                       509
```

<210> SEQ ID NO 13
<211> LENGTH: 329
<212> TYPE: DNA
<213> ORGANISM: Fragaria x ananassa

<400> SEQUENCE: 13

```
tgtagcggag ggattgtttt gtcatttcaa aactgaggga cttttttttt tattgaaatt      60
aaactgaggg ccttgcaagc cgtaggcgtt ggtactggac ggtgccgttt tctttgatcg     120
aagttttttat ggcaagggt ttaattgtcc tttcaaaaat gttagaagtg aaatttgggt     180
cagatggatg aaggttttct tctgtccata tatacgagtg tattatgttt cgtcgatgta     240
tcgatgattt atattaaatt tcagattttta atttgagac atgaaaaaca tttataattt     300
aagtgatttt gtgtttctag ccttatagt                                       329
```

<210> SEQ ID NO 14
<211> LENGTH: 474
<212> TYPE: DNA
<213> ORGANISM: Fragaria x ananassa

<400> SEQUENCE: 14

```
agtgctatgg aatatctctt cggttcaacc tttgtgtgca agactattaa tgctgcaaag      60
gaggtgagag gttgattatc gtgctgtagg ctgattatat agtattgtcc ttttaaacac     120
ttgtaatcta agcaggaaag cggcatgacc caatctggtt ctctatgaat gtttcctagg     180
ttgcttttaa cagggaagtt cgtaccctag tgtcactctt gaaggtgata tcttccagcc     240
cagtggtctt ttgactggtg gaagccgcaa gtaagccact gttctttttc ctccagttta     300
gatttcatgc tttaccccct tcctcttgag tatatctgtt gttagctctc tctgactaat     360
tttccatact tgtgttgtcc ttatcattta tcaattcaaa gtacatatac ttctagccag     420
ttttccttct aaagcaaaaa tttcctgtca caggggtggg ggagatctgt taag           474
```

<210> SEQ ID NO 15
<211> LENGTH: 442
<212> TYPE: DNA
<213> ORGANISM: Fragaria x ananassa

<400> SEQUENCE: 15

```
taggtgatat ttgacgtgca agtgtccaaa ataatctcat aaggcctaac tcccccatcg      60
tcacaatttg accatcaaac tatctccagc gctacctgtt gtcggcaccc tctaccgacg     120
ttatttcaca accatttaa ttaacgttcg atttgtttca gtgaaaaaca aacagttggt     180
agtaaaagat catggtaaaa agcagactgc gtggtggggt ggatgtacac aacgcggagt     240
agaacgctta agttttttca caccactaat aatatattat acatattata taatacaaaa     300
cctgtaatta taaatataca taatatattc ttaagaaaac tttgcgaggt aaaagtggtg     360
gcggcaaggc actttgagtg attagaattg ggaggttttg gtggtggatg acactgaata     420
tagtgccgga tgcttgccgg gt                                              442
```

<210> SEQ ID NO 16
<211> LENGTH: 332
<212> TYPE: DNA
<213> ORGANISM: Fragaria x ananassa

<400> SEQUENCE: 16

```
aaattgtttc catatgatac ggttcaacat gacacttaca tagttacatt agcatagaag      60
tcaacattgc ctctctttct cacaactgat caaactctac ctgatcaggc aggccaatca     120
agagaggatt tgactgcatt tcagcaaaat aagcacatat gcaacaccct atgcacatat     180
acaagaagtg gcacattgcc ttcacatttg cctaaaagta cataaaacta acagaagcat     240
ccatgaaagc tccatggcaa ccacttctca actccattgc ctagttaaac aatgtagatc     300
ataattaaaa cagatatttg aggagcagga aa                                   332
```

<210> SEQ ID NO 17
<211> LENGTH: 471
<212> TYPE: DNA
<213> ORGANISM: Fragaria x ananassa

<400> SEQUENCE: 17

```
caaaccgggt ttagacttgc tacgatcaag ttgttcttca atctgctctg ccattctccc      60
tacatcatag acacccggaa agtgtgaggg ctaatgtgat tgccaacaat ataattgatg     120
ctttgaatag aggggtgaac ttggatgaca aggagagtaa ggatagtggt gtttcgcatt     180
tgactgattt gaattgggag gttttggtgg tggatgacac tgaatatagt gccggatgct     240
tgccgggtgg gaagattgtg gtctgctcag ggctgctcaa gcattatttt agtgatgcgg     300
```

```
agatagctat ggtaattgct catgaggtac gatgactagt tgtgtagtgt ttctgttcaa      360
agtgctaaaa caatgtgggc tgctaacttc tcctctgtct tgtgattgca agctaggttg      420
ggcatactgt ggctcgacac caagctgagt tagtcacaaa gttcctgtgg c               471

<210> SEQ ID NO 18
<211> LENGTH: 784
<212> TYPE: DNA
<213> ORGANISM: Fragaria x ananassa

<400> SEQUENCE: 18
tgtagcggag ggattgtttt gtcatttcaa aactgaggga cttttttttt attgaaatta       60
aactgagggc cttgcaagcc gtaggcgttg gtactggacg gtgccgtttt ctttgatcga      120 agttttatg gcaaggggtt taattgtcct ttcaaaaatg ttagaagtga aatttgggtc      180
agatggatga aggttttctt ctgtccatat atacgagtgt attatgtttc gtcgatgtat      240
cgatgattta tattaaattt cagattttaa ttttgagaca tgaaaaacat ttataattta      300
agtgattttg tgtttctagc cttatagtgc gtatgaatga gacacaacgt acaaaaaagt      360
tgagataaga aaatgaccca taaattattt tggtttttaat ttatgtaagc gatattttta      420
ggttggttga ttatgaattt atgtacatta aaattcaaaa tattttttg gcacattaga      480 ttgtaaactt gaatcaatag tacttgacgt cgttagcatg attgaattgt caatgttgt      540 atattttgaa aggtaaaaag gtacctctct tcacttcatc tttttttgtct ctaaaccaca      600 ccaagactt gcgcaaagcc ctccatcttt acatcaaatg gtgatattct aagtcgcata      660
ccaaaacccc gatctccaag actcgactcc caaatctgga gatggaggtg acaacacgac      720
tagaatcaca gctttggtac tatcatgaca ataagttgaa caactttggt cgtctgggta      780
tgct                                                                   784

<210> SEQ ID NO 19
<211> LENGTH: 488
<212> TYPE: DNA
<213> ORGANISM: Fragaria x ananassa

<400> SEQUENCE: 19
gaaaacccca tcatctttaa tcctttgctg aggggaagca caagggctca acagctataa       60
cattgagcaa ctactatagt tagtcctgtg attggaagtg ccaagggtct tcaaaataac      120
cggggcaatc tatggccatg gttctatgta tatacataat cctctatcct agttatgcta      180
ccaaatatgt tctgagacat aatcgttctt ctgttgctcg gaacaatgca gaaaacttaa      240
aatagtaaaa gtgttgttat agaatctcct caaaatttta gaccattta gggaaattct      300 atcagtgttt caatcgttag acacttcaag tcctagtata ctaatccaaa agcctcacta      360
caaaatacat gaagacatt tacatgcgac catactagcc ttcctctatc agaacgaacc      420
aacactaaga gagcatcat aggatacata atcctctatc cgtaaacaaa tgacaatcag      480
aagaaaca                                                              488

<210> SEQ ID NO 20
<211> LENGTH: 18
<212> TYPE: DNA
<213> ORGANISM: Artificial Sequence
<220> FEATURE:
<223> OTHER INFORMATION: Synthetic DNA

<400> SEQUENCE: 20
cacgatggat ccagtgca                                                     18
```

```
<210> SEQ ID NO 21
<211> LENGTH: 16
<212> TYPE: DNA
<213> ORGANISM: Artificial Sequence
<220> FEATURE:
<223> OTHER INFORMATION: Synthetic DNA

<400> SEQUENCE: 21
ctggatccat cgtgca                                                   16

<210> SEQ ID NO 22
<211> LENGTH: 16
<212> TYPE: DNA
<213> ORGANISM: Artificial Sequence
<220> FEATURE:
<223> OTHER INFORMATION: Synthetic DNA

<400> SEQUENCE: 22
gatggatcca gtgcag                                                   16

<210> SEQ ID NO 23
<211> LENGTH: 22
<212> TYPE: DNA
<213> ORGANISM: Artificial Sequence
<220> FEATURE:
<223> OTHER INFORMATION: Synthetic DNA

<400> SEQUENCE: 23
acacatatat gaatcggagc ca                                            22

<210> SEQ ID NO 24
<211> LENGTH: 20
<212> TYPE: DNA
<213> ORGANISM: Artificial Sequence
<220> FEATURE:
<223> OTHER INFORMATION: Synthetic DNA

<400> SEQUENCE: 24
gctcaagatg ctcaatcgaa                                               20

<210> SEQ ID NO 25
<211> LENGTH: 20
<212> TYPE: DNA
<213> ORGANISM: Artificial Sequence
<220> FEATURE:
<223> OTHER INFORMATION: Synthetic DNA

<400> SEQUENCE: 25
ctttgacgcc tactgcatta                                               20

<210> SEQ ID NO 26
<211> LENGTH: 20
<212> TYPE: DNA
<213> ORGANISM: Artificial Sequence
<220> FEATURE:
<223> OTHER INFORMATION: Synthetic DNA

<400> SEQUENCE: 26
ggttgggctt cgttaaatct                                               20
```